US008771326B2

(12) United States Patent
Myeong et al.

(10) Patent No.: US 8,771,326 B2
(45) Date of Patent: *Jul. 8, 2014

(54) ADIPOSE RESOLVE APPARATUS FOR LOW-POWER LASER

(75) Inventors: Hyeon Seong Myeong, Seoul (KR); Anna Brazier, Vancouver (CA)

(73) Assignee: Yolo Medical Inc. (CA)

( * ) Notice: Subject to any disclaimer, the term of this patent is extended or adjusted under 35 U.S.C. 154(b) by 1885 days.

This patent is subject to a terminal disclaimer.

(21) Appl. No.: 11/860,457

(22) Filed: Sep. 24, 2007

(65) Prior Publication Data

US 2008/0119831 A1    May 22, 2008

Related U.S. Application Data

(63) Continuation-in-part of application No. 11/577,356, filed as application No. PCT/KR2006/000694 on Feb. 28, 2006, now Pat. No. 7,959,656.

(30) Foreign Application Priority Data

Mar. 2, 2005 (KR) .................. 10-2005-0017330
Feb. 17, 2006 (KR) .................. 10-2006-0015778

(51) Int. Cl.
A61N 5/067    (2006.01)

(52) U.S. Cl.
USPC .............................................. 607/89; 607/88

(58) Field of Classification Search
USPC .................. 67/88–94; 606/3, 7–12, 16–18
See application file for complete search history.

(56) References Cited

U.S. PATENT DOCUMENTS

| 4,653,495 A | 3/1987 | Nanaumi |
| 4,905,690 A | 3/1990 | Ohshiro et al. |
| 4,930,504 A * | 6/1990 | Diamantopoulos et al. .... 607/88 |

(Continued)

FOREIGN PATENT DOCUMENTS

| KR | 20-270882 | 4/2002 |
| KR | 20-274266 | 5/2002 |

(Continued)

OTHER PUBLICATIONS

Neira, R. et al., "Fat Liquefaction: Effect of Low-Level Laser Energy on Adipose Tissue," *Plastic and Reconstructive Surgery* (2002), 110(3):912-922.

*Primary Examiner* — Ahmed Farah
(74) *Attorney, Agent, or Firm* — Thomas A. Runk; Fulwider Patton LLP

(57) ABSTRACT

A lipolysis system configured for contacting and providing low-power laser irradiation to a plurality of targeted portions of a subject's body surface for the purpose of liquefying fats in subcutaneous regions underlying the targeted body surface portions, and methods for the use of the lipolysis system. The lipolysis system comprises: (a) a first laser applicator comprising a plurality of low-power laser diodes selected for emission of power outputs in the range comprising about 10 mW to about 100 mW with light waves in the range of 635 nm to 680 nm, (b) a second laser applicator comprising at least one low-power laser diode selected for emission of power outputs in the range comprising about 10 mW to about 100 mW with light waves in the range of 635 nm to 680 nm, and (c) a laser control device configured for controllably communicating and cooperating with said first laser applicator and said second laser applicator.

7 Claims, 18 Drawing Sheets

(56) References Cited

U.S. PATENT DOCUMENTS

| | | | |
|---|---|---|---|
| 5,150,704 A | 9/1992 | Tatebayashi et al. | |
| 5,409,482 A * | 4/1995 | Diamantopoulos | 606/13 |
| 5,474,528 A | 12/1995 | Meserol | |
| 5,507,790 A | 4/1996 | Weiss | |
| 5,755,752 A | 5/1998 | Segal | |
| 5,879,376 A | 3/1999 | Miller | |
| 6,024,760 A | 2/2000 | Marchesi | |
| 6,063,108 A | 5/2000 | Salansky et al. | |
| 6,074,411 A | 6/2000 | Lai et al. | |
| 6,106,516 A | 8/2000 | Massengill | |
| 6,264,649 B1 * | 7/2001 | Whitcroft et al. | 606/9 |
| 6,273,884 B1 | 8/2001 | Altshuler et al. | |
| 6,273,885 B1 | 8/2001 | Koop et al. | |
| 6,306,130 B1 * | 10/2001 | Anderson et al. | 606/27 |
| 6,322,584 B2 | 11/2001 | Ingle et al. | |
| 6,413,267 B1 | 7/2002 | Dumoulin-White et al. | |
| 6,461,866 B1 | 10/2002 | Whitehurst | |
| 6,517,532 B1 | 2/2003 | Altshuler et al. | |
| 6,530,920 B1 | 3/2003 | Whitcroft et al. | |
| 6,582,454 B2 | 6/2003 | Yayama | |
| 6,605,079 B2 | 8/2003 | Tucek et al. | |
| 6,605,080 B1 | 8/2003 | Altshuler et al. | |
| 6,645,230 B2 | 11/2003 | Whitehurst | |
| 6,673,096 B2 | 1/2004 | Lach | |
| 6,676,654 B1 | 1/2004 | Balle-Petersen et al. | |
| 6,676,655 B2 | 1/2004 | McDaniel | |
| 6,746,473 B2 | 6/2004 | Shanks et al. | |
| 6,887,260 B1 | 5/2005 | McDaniel | |
| 7,033,381 B1 * | 4/2006 | Larsen | 607/88 |
| 7,060,061 B2 | 6/2006 | Altshuler et al. | |
| 7,090,670 B2 | 8/2006 | Sink | |
| 7,118,588 B2 | 10/2006 | Tucek et al. | |
| 7,241,291 B2 * | 7/2007 | Kreindel et al. | 606/9 |
| 7,431,719 B2 | 10/2008 | Altshuler et al. | |
| 7,524,317 B2 * | 4/2009 | Gruzdev et al. | 606/9 |
| 7,959,656 B2 * | 6/2011 | Myeong et al. | 607/88 |
| 2001/0011585 A1 | 8/2001 | Cassidy et al. | |
| 2003/0199859 A1 * | 10/2003 | Altshuler et al. | 606/9 |
| 2004/0006378 A1 | 1/2004 | Shanks et al. | |
| 2004/0093042 A1 | 5/2004 | Altshuler et al. | |
| 2004/0093047 A1 | 5/2004 | Lach | |
| 2004/0116984 A1 | 6/2004 | Spooner et al. | |
| 2004/0181210 A1 | 9/2004 | Shellman | |
| 2004/0236252 A1 | 11/2004 | Muzzi et al. | |
| 2005/0203594 A1 | 9/2005 | Lim et al. | |
| 2006/0095099 A1 | 5/2006 | Shanks et al. | |
| 2006/0206176 A1 | 9/2006 | Shanks et al. | |
| 2006/0224148 A1 | 10/2006 | Cho et al. | |
| 2007/0073367 A1 | 3/2007 | Jones et al. | |
| 2008/0108982 A1 | 5/2008 | Barolet et al. | |

FOREIGN PATENT DOCUMENTS

| | | |
|---|---|---|
| KR | 20-302173 | 1/2003 |
| KR | 20030000151 B1 | 1/2003 |
| WO | WO 2006/093384 | 9/2006 |

* cited by examiner

Fig. 10
(a) 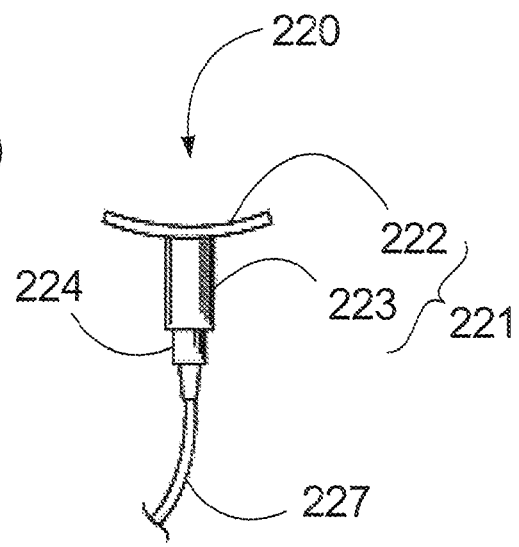
(b) 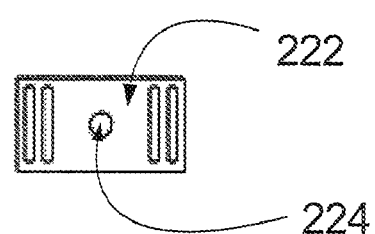
(c) 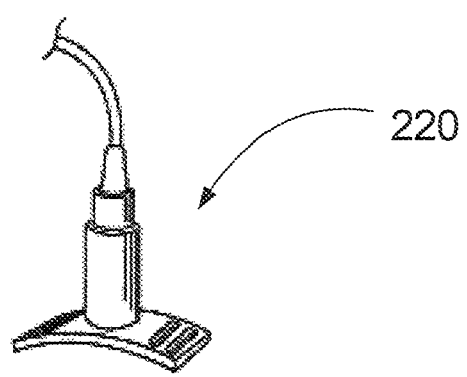

ADIPOSE RESOLVE APPARATUS FOR LOW-POWER LASER

CROSS-REFERENCE TO RELATED APPLICATIONS

This application is a continuation-in-part of U.S. application Ser. No. 11/577,356 filed on Apr. 17, 2007, which is a national phase filing under 35 U.S.C. §371 of international application number PCT/KR2006/000694, filed Feb. 28, 2006, which claims priority from Korean application number 10-2006-0015778, filed Feb. 17, 2006, and Korean application number 10-2005-0017330, filed Mar. 2, 2005. The entire content of each of these prior applications is incorporated herein by reference in its entirety.

TECHNICAL FIELD

The present invention relates to low-power laser irradiation of skin surfaces for lipolysis of underlying adipose cells. More particularly, this invention relates to low-power laser applicators, systems comprising the laser applicators, and methods for their use in providing lipolysis treatments.

BACKGROUND OF THE INVENTION

Various apparatuses are known for providing a curative effect by irradiating spots on a patient's body with low-power insertable laser devices. Such apparatus are generally configured with one or more laser diodes configured for emitting outputs in the range of 5 mW to 10 mW and wavelengths in the range of 635 nm to 650 nm, and a low power laser diode driver for arbitrarily adjusting the amount of laser beam emitted from the on or more laser diodes.

For example, Korean Utility Model No. 302173 discloses an electric mat for uniformly emitting a laser beam through a low power laser diode. Korean Utility Model No. 270882 discloses a waist belt including a laser generator having a laser diode for emitting laser light having a wavelength of 580~980 nm to stimulate the lumbar, thereby performing finger-pressure treatment and therefore medical treatment of a disc. Korean Utility Model No. 274266 discloses a laser for medical treatment and an LED blanket capable of widening a curative range, for example, irradiation of spots on the body suitable for acupuncture, chronic article rheumatism, frozen shoulder, lumbago, cervical vertebral sprain, gout, wrench, bruising, arthritis, stress gastritis, and so on. Korean Patent No. 457964, issued to the present applicant, discloses a laser beam radiator capable of non-invasively irradiating blood in a blood vessel with a laser beam according to a position and a thickness of the blood vessel by adjusting a distance of the laser beam condensed through an optical lens, activating metabolism of a cell by stimulating a blood cell using a laser beam, increasing formation of capillary vessels to improve blood circulation, and increasing speed of tissue treatment to activate living organisms.

While another laser apparatus using a laser beam disposed in an array for providing use convenience is proposed to be adapted to various soft materials such as a chair, a hat, a bed, a belt, and so on, when the laser beam is disposed in the soft materials in an array, a red laser capable of being output appropriately to non-invasively break down fat (about, more than 30 mW) should be used. However, since the red laser requires a separate radiation structure, there is no way of breaking down fat by non-invasively irradiating a human body.

Meanwhile, in order to effectively treat obesity using a laser, Neira et al. (2002, Plastic and Reconstructive Surgery 110(3): 912-922) disclose a process for liquefying fat by waving a low-power laser back and forth six inches above a subject's abdomen and then removing the liquefied fat with a surgical liposuction i.e., lipectomy procedure. Neira et al.'s paper is based on a test in which lasers having a wavelength of 635 nm, an output of 10 mW, and a total energy of $1.2J/cm^2$, $2.4J/cm^2$ and $3.6J/cm^2$ are radiated onto adipose tissue extracted from 12 healthy women. As a result of the test, 4 minutes after laser exposure, 80% of the fat in the adipose cells is discharged, and 6 minutes after the laser exposure, 99% is discharged. It was reported that energy of the low power laser acts to open a cell wall to discharge fat from the interior to the exterior of the adipose cell. Then, the discharged fat is gathered in a space between the adipose tissues. Using the fat liquefaction effect of the red laser on the basis of the test, suction lipectomy using a laser, in which the human body is irradiated from outside to break down fat and discharge the broken down fat from the body using a cannular (fine pipe), has been proposed.

Various methods of non-invasively irradiating skin covering a fatty area of a treatment target with a red laser beam to break down the fat of the adipose cells have been attempted. In order to irradiate a wider area for a short time, a device for forming a red laser beam with a line shape to scan the treatment target has been developed and put on the market. However, it is difficult to input a power of 10 mW and an energy density of $3.6J/cm^2$ required for lipolysis in the human body, thereby obtaining little practical effect.

SUMMARY OF THE INVENTION

The exemplary embodiments of the present invention are directed to laser applicators, systems comprising the laser applicators, and methods for their use for liquefaction of fats in adipose cells for removal into interstitial spaces wherefrom they are removed from a subject's body by their normal physiological processes.

According to one exemplary embodiment, there is provided a laser applicator having at least one low-power light-emitting laser diode. A suitable low-power light-emitting laser diode is one that emits power outputs in the range comprising about 10 mW to about 100 mW with light waves in the range of 635 nm to 680 nm. The laser applicator is configured for contacting a subject's body surface for application of low-power laser irradiation. The laser applicator is configured to communicate and cooperate with a laser control device comprising a power supply device, circuitry interconnecting software-controllable electronic devices configured for at least one of generating, transmitting, recording, processing, storing and reporting electronic signals useful for manipulable modulation of the output from the power supply device for generation of laser light waves. The low-power laser irradiation causes liquefaction of fats in adipose cells in the subcutaneous portions of the subject's body underlying the surface contacted by the laser applicator. The liquefied fat is discharged from the adipose cells into the interstitial areas between the cells from which it is absorbed by the subject's lymphatic system and removed from their body with their normal physiological processes.

According to one aspect, the laser applicator comprises a plurality of low-power light-emitting diodes.

According to another aspect, the laser applicator is provided with a plurality of low-power light-emitting diodes each selected for emission of power outputs in the range comprising about 10 mW to about 100 mW with light waves in the range of 635 nm to 680 nm, and a plurality of medium power laser diodes having power outputs in the range of about 80 mW to about 160 mW with light waves in the range of 780 nm to 980 nm.

According to another aspect, the laser applicator comprises a printed circuit board provided with a power connector for communicating with a controller device, a contact plate formed of a hard plate configured for cooperating with the PCB and having at least one transparent window or a lens disposed at one side surface, at least on low-power light-emitting laser diode inserted into the at least one transparent window or lens disposed on the contact plate and electrically connected to the PCB; and a framework or alternatively, a housing for accommodating and retaining therein the laser printed circuit board, contact plate and laser diode. The housing is suitable configured for contacting the at least one transparent window or lens of the contact plate in close contact with the skin during application of laser irradiation of the skin and underlying subcutaneous region.

According to a further aspect, the contact plate may comprise a flexible material.

According to a yet further aspect, a plate of heat-absorbing material may be interposed the contact plate and the printed circuit board. The plate of heat-absorbing material may be configured to communicate and cooperate with a cooling device.

According to another aspect, the surface of the contact plate may be coated with a thermal interface material.

According to another exemplary embodiment of the present invention, there is provided a lipolysis system comprising at least one laser applicator provided with at least one low-power laser diode selected for emission of power outputs in the range comprising about 10 mW to about 100 mW with light waves in the range of 635 nm to 680 nm, and a laser control device provided with hardware, circuitry and software configured for at least one of generating, transmitting, recording, processing, storing and reporting electronic signals useful for manipulable modulation of the output from the power supply device for generation of laser light waves. The at least one applicator is configured for contacting a portion of a subject's body surface for controllably and manipulably providing laser light irradiation thereto for the purpose of liquefying fats in adipose cells in the subcutaneous region underlying the portion of the subject's body surfaces contacted by the laser applicator.

According to one aspect, the laser applicator is provided with a plurality of low-power laser diodes each selected for emission of power outputs in the range comprising about 10 mW to about 100 mW with light waves in the range of 635 nm to 680 nm.

According to another aspect, the laser applicator is provided with a plurality of low-power light-emitting diodes each selected for emission of power outputs in the range comprising about 10 mW to about 100 mW with light waves in the range of 635 nm to 680 nm, and a plurality of medium-power laser diodes each having power outputs in the range of about 80 mW to about 160 mW with light waves in the range of 780 nm to 980 nm.

According to another aspect, the laser applicator housing may be configured to contact a larger portion of a subject's body surface such as an abdomen, the lower back area, hips, and buttocks. The housing and contact plate provided in this embodiment are suitably concave. The contact plate may optionally comprise a flexible material.

According to yet another aspect, the laser applicator housing or alternatively the framework, may be provided with hinges on its opposite ends thereby making it possible to interlink two or more such hinged laser applicators together. Accordingly, the two or more interlinked laser applicators may be controllably maneuvered to provide excellent contact of larger portions of a subject's body surface with the contact plates having disposed therein laser diodes.

According to another exemplary embodiment of the present invention, there are provided methods for the use of the lipolysis systems of the present invention for liquefying fats in subcutaneous adipose cells. An operator contacts the contact plate of the at least one laser applicator with a target portion of a subject's body surface after which the operator manipulates the control device to provide laser light irradiation of the target portion of the subject's body portion for a selected period of time during which the laser light causes liquefaction of fats in adipose cells in the subcutaneous region underlying the target body portion. The liquefied fats are discharged from the adipose cells into the interstitial spaces wherefrom the liquified fats are removed from the subcutaneous regions underlying the target portions by the subject's lymphatic system. It is suitable during a lipolysis treatment session to contact the at least one laser applicator with multiple target portions of a subject's body surface for application of laser irradiation thereto.

According to another exemplary embodiment of the present invention, there is provided a vacuum suction device configured to sealably engage and cooperate therewith a laser applicator of the present invention. The vacuum suction device is suitably configured with an inner bowl-shaped chamber having an outer rim configured for sealingly engaging a target portion of a subject's body surface. The apex of the bowl-shaped chamber is configured to sealingly engage and communicate with the contact plate of the laser applicator, and to transmit therethrough laser irradiation generated by the at least one laser diode of the laser applicator. The vacuum suction device is interconnected to a controllable vacuum pump.

According to one aspect, the vacuum suction device is configured to sealingly engage and cooperate with a laser-generating device comprising a low-power laser diode selected for emission of power outputs in the range comprising about 10 mW to about 100 mW with light waves in the range of 635 nm to 680 nm.

According to another aspect, the vacuum suction device is provided with at least one pressure release aperture configured for engagement and disengagement by an operator's finger.

According to another exemplary embodiment of the present invention, there is provided a lipolaser system comprising a vacuum suction device configured to cooperate with a laser applicator of the present invention or alternatively with a laser generating device, an exemplary laser applicator of present invention or alternatively a laser generating device, and a controllable vacuum pump cooperatively interconnected to the vacuum suction device.

According to one aspect, the vacuum pump is controllably and manipulably interconnected to a plurality of vacuum suction devices.

According to another exemplary embodiment, there are provided methods for the provided methods for the use of the lipolysis systems comprising the vacuum suction devices of the present invention for liquefying fats in subcutaneous adipose cells. An operator contacts the outer rim of the vacuum suction device with a target portion of a subject's body surface after which the operator activates the vacuum pump and manipulates the laser control device to provide laser light irradiation of the target portion of the subject's body portion for a selected period of time during which the laser light causes liquefaction of fats in adipose cells in the subcutaneous region underlying the target body portion. The liquefied fats are discharged from the adipose cells into the interstitial spaces wherefrom the liquified fats are removed from the subcutaneous regions underlying the target portions by the subject's lymphatic system. It is suitable during a lipolysis treatment session to contact the at least one laser applicator with multiple target portions of a subject's body surface for application of laser irradiation thereto.

According to one aspect, an operator may impose and release suction force within the vacuum suction device by engaging and disengaging the pressure release aperture with their finger. The vacuum suction device may be moved about a subject's body surface while the pressure release aperture is disengaged.

BRIEF DESCRIPTION OF THE DRAWINGS

The present invention will be described in conjunction with reference to the following drawings, in which:

FIG. 10(a) is a side view of one type of laser applicator of the lipolysis system shown in FIG. 9;

FIG. 10(b) is an end view of the laser applicator shown in FIG. 10(a);

FIG. 10(c) is a perspective view of the laser applicator shown in FIG. 10(a);

DETAILED DESCRIPTION OF THE INVENTION

Exemplary embodiments of the present invention provide laser applicators for contacting and controllably irradiating portions of a subject's body surfaces with low-power lasers, systems comprising one or more of the laser applicators cooperating with a suitable control devices for controllably generating laser irradiation from the laser applicators, and methods for the use of the systems for liquefaction of fat in adipose cells underlying the body surfaces for removal from the irradiated portions by the subject's physiological processes.

Figure 1:
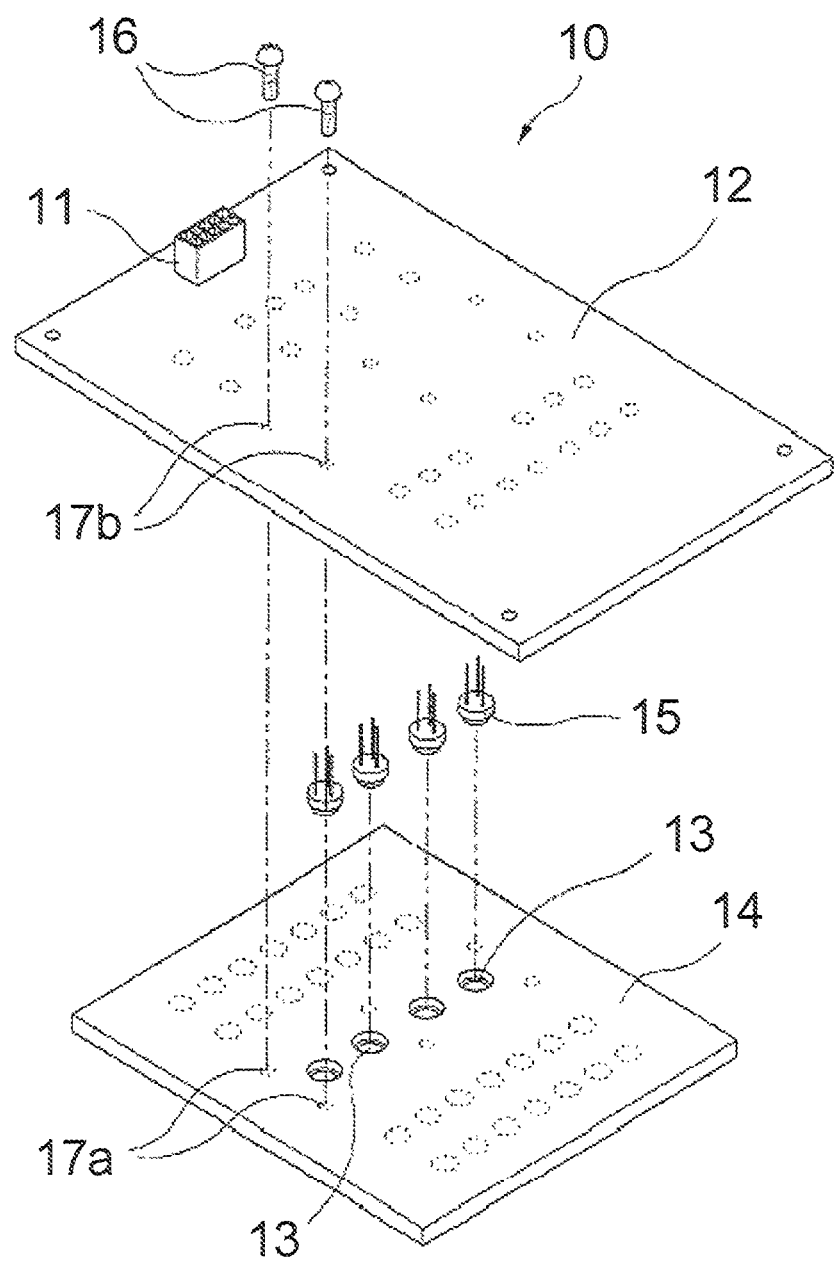
FIG. 1 is an exploded perspective view of a laser applicator of an exemplary lipolysis system according to one embodiment of the present invention.

An exemplary laser-applicator 10 of the present invention is illustrated in FIG. 1. The laser applicator 10 generally comprises a printed circuit board (PCB) 12 provided with a power connector 11 for receiving power, and a contact plate 14 configured to communicate and cooperate with the PCB 12. The contact plate 14 is provided with one or more selectively spaced-apart transparent windows or alternatively lenses 13 disposed on the surface opposite the surface that contacts the PCB 12. One or more laser diodes 15 are inserted into selected transparent windows or lenses 13 disposed on the contact plate 14, and is electrically connected to the PCB 12. A plurality of fastening holes 17a and 17b are provided at selected locations on the PCB board 12 and the contact plate 14 to enable securing of the PCB 12 to the contact plate 14 with a plurality of fasteners 16. As shown in FIG. 1, the laser applicator 10 may be assembled by inserting the laser diodes 15 into the transparent windows or lenses 13 of the contact plate 14, then securing the contact plate 14 to the PCB 12 with a plurality of the fasteners 16. Although FIG. 1 shows the laser applicator 10 configured with four laser diodes 15, it is within the scope of this invention to provide laser applicators having one laser diode or alternatively, a selectable plurality of laser diodes. The laser applicator 10 is interconnectable through the power connector 11 to a laser control device (not shown) comprising a power supply device, circuitry interconnecting software-controllable electronic devices configured for at least one of generating, transmitting, recording, processing, storing and reporting electronic signals useful for manipulable modulation of the output from the power supply device for generation of laser light waves.

It is suitable to encase the laser applicator 10 within a housing structure (not shown) configured to expose at least the transparent windows or lenses of the contact plate 14, and to provide suitable contact for the contact plate 14 with a subject's body surface. It is preferable that the housing structure is also configured for graspability and ease-of-handling by an operator and for a subject's comfort when the laser applicator 10 is in contact with a portion of their body surface. Alternatively, as illustrated in FIG. 2, a laser applicator according to the present invention may comprise a housing or framework 30 provided for containing a PCB (not shown) cooperatively assembled with a contact plate 14 configured with a large plurality of laser diodes 15.

Figure 2:
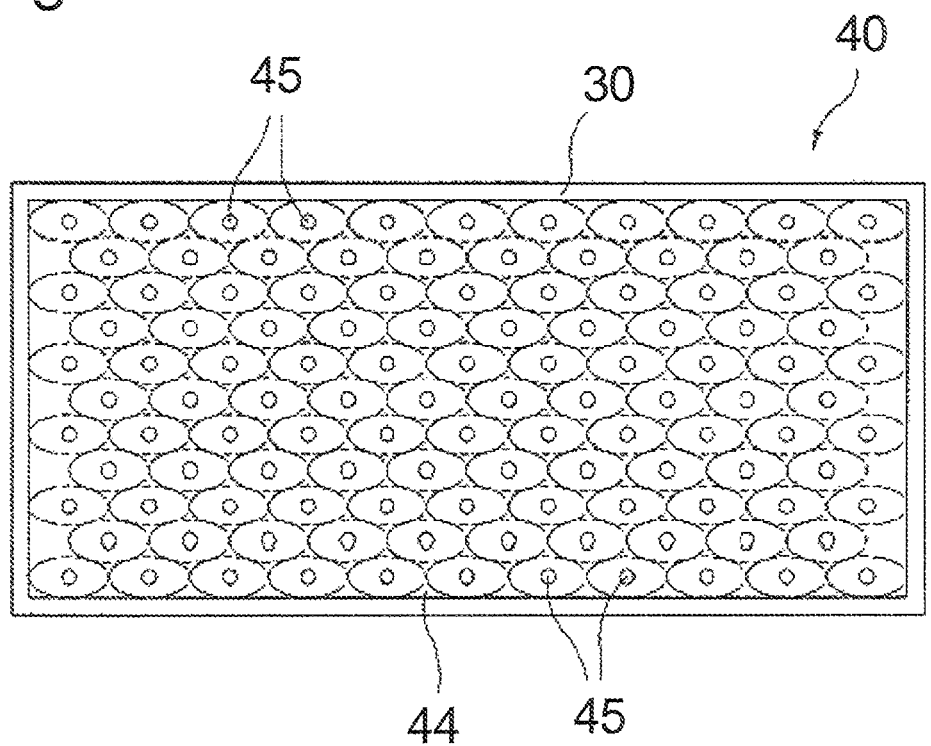
FIG. 2 is a plan view of a laser irradiation distribution range of an exemplary laser applicator according to another embodiment of the present invention.

While the plurality of laser diodes 15 shown in FIGS. 1 and 2 are uniformly disposed within the contact plate 14, it is also within the scope of the present invention to dispose a selected number of laser diodes 15 in an irregular pattern about the contact plate 14. Furthermore, although an elongate contact plate 14 is illustrated in FIGS. 1 and 2, it is also within the scope of the present invention to provide contact plates having alternative shapes such as circular, elliptical, sigmoidal, obround, gibbous and the like, configured to enhance the comfort of a subject when the laser applicator 10 is contacting a portion of their body surface.

Suitable laser diodes for incorporation into the laser applicators of the present invention are capable of producing power outputs in the range comprising about 10 mW to about 100 mW with light waves in the range of 635 nm to 680 nm, i.e., commonly referred to by those skilled in this art as low-power light-emitting laser diodes. When one or more of such low-power laser diodes is/are contacted with a subject's body surface, the emitted light waves will penetrate through the epidermal and dermal skin layers into the subcutaneous regions which are primarily composed of adipose cells. The energy of low-power light waves penetrating into the adipose cells causes liquefaction of solid and semi-solid fat deposits contained in the adipose cells. The liquefied fats are then easily translocated out of the adipose cells into the interstitial spaces from where they are removed by the subject's lymphatic system and discharged from the subject's body by their normal physiological processes.

A possible consequence of providing arrays with large pluralities of low-power laser diodes is that considerable amounts of heat may be generated from the laser diodes during prolonged application of laser light energy to a subject's body portion thereby causing some discomfort. Therefore, it is within the scope of the present invention to provide a plate of heat-absorbing material interposed the contact plate 14 and the PCB 12 to absorb heat generated by the bases of the low-power laser diodes, and configured to disperse the heat toward and from the rear of the laser applicator. Alternatively, the plate of heat absorbing material may be configured to communicate and cooperate with a cooling device for controllably removing heat generated by the low-power laser diodes while cooling the contact plate 14. Alternatively, the surface of the contact plate 14 opposite the PCB board 12 may be coated with a thermal interface material.

Figure 3:
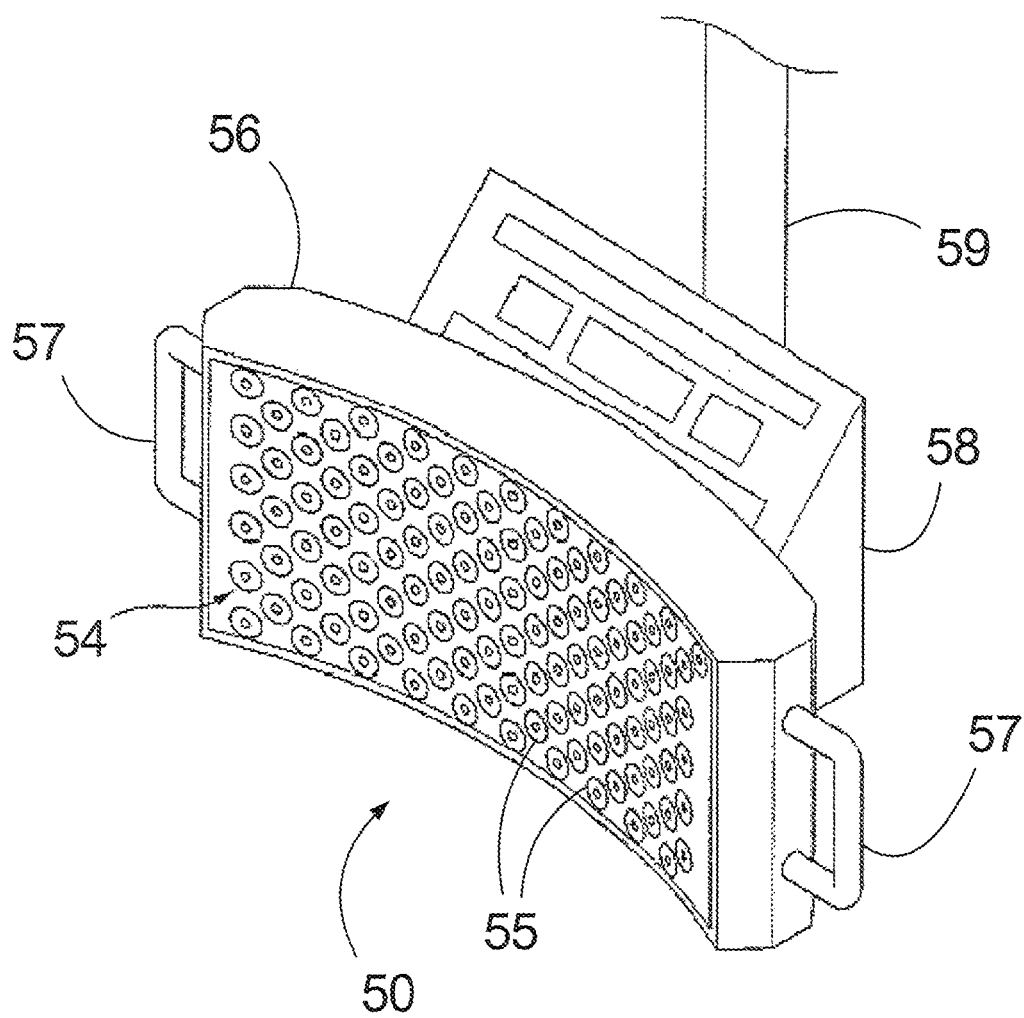
FIG. 3 is a perspective view of an exemplary laser applicator system according to the present invention.

It is particularly useful to configure a laser applicator comprising at least one extended array of closely placed together plurality of low-power laser diodes for contacting a subject's body surface thereby enabling the irradiation of larger surface areas. The consequence is a more uniform irradiation of larger areas of adipose cells resulting in more substantial amounts of fat liquefaction and removal from the body portions contacted by the laser applicator, thus making it possible to selectively reduce the extent of fat-induced protuberances about a subject's body. FIG. 3 illustrates another exemplary laser applicator 50 provided with a concave contact plate 54 fitted into concave curvilinear framework 56 configured to at least partially encircle larger areas of a subject's body such as the abdomen, lower hips, buttocks, and upper thigh areas. The opposite ends of the framework 56 are provided with handles 57, to enable easy handling and positioning of the laser applicator 50 about the subject's body portions by an operator. For such laser applicators, it is suitable for the contact plate 54 to comprise a flexible material that is capable of conforming to the contours of the subject's body portions onto which the laser applicator is positioned. Alternatively, the contact plate 54 may comprise a stiff material that may be molded into a selected configuration suitable for application only to a selected target body portion. The exemplary laser applicator 50 illustrated in FIG. 3 may be placed and positioned by an operator onto a subject who is in a prone position lying on their back or alternatively, on their stomach. However, it is optional to provide a vertical support 59 fitted with a vertically adjustable positioning device 58 configured to engage the laser applicator 50. The subject can then in a standing position contact a selected body portion with the laser applicator 50 after the positioning device 58 has been adjusted to provide optional contact between the subject's body portion and the laser applicator 10. Those skilled in these arts will understand that the vertically adjustable positioning device 58 may be optionally provided with a pivoting component (not shown) for enabling the rotation of the laser applicator from a horizontal plane to a vertical plane. It is also within the scope of the present invention to incorporate a laser control device components into the positioning device 58.

Figure 4:
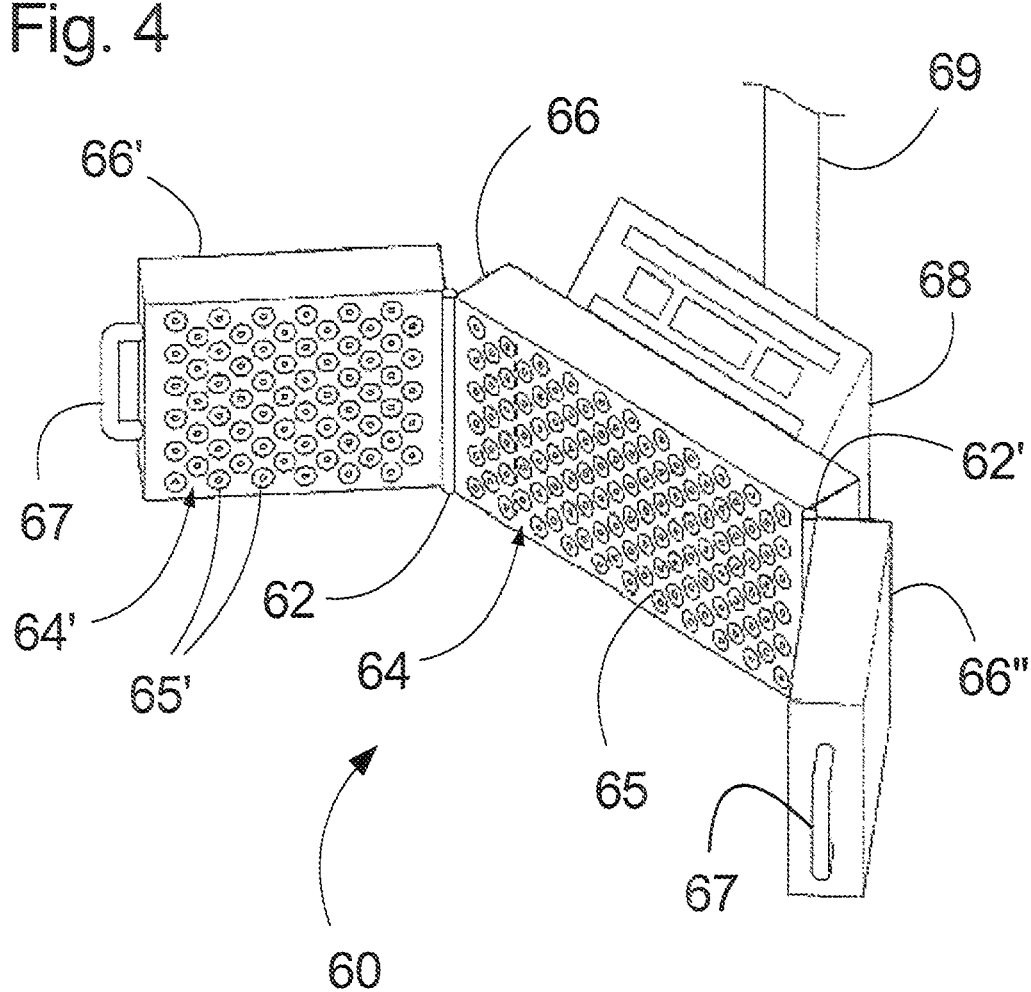
FIG. 4 is a perspective view of another exemplary laser applicator system according to the present invention.

FIG. 4 is a perspective view of an alternative embodiment of a laser applicator 60 comprising three interconnected hinged sections 66, 66', 66" that can be adjusted to encompass larger portions of a subject's body surface regardless of the extent of protuberations caused by excessive accumulations of solid and semi-solid fats in the adipose cells underlying the larger portions of the body surface. In this exemplary embodiment, a primary section 66 comprising a housing fitted with a flat elongate contact plate 64 having a plurality of laser diodes 65, is provided with a hinge 62 disposed at each of its opposite ends. A first secondary section 66' is fitted with a flat contact plate 64' having a plurality of laser diodes 65', and has one end configured for hinged communication and cooperation with a first hinge 62. A second secondary section 66" also fitted with a flat contact plate (not visible in this view) having a plurality of laser diodes (not visible in this view), has one end configured for hinged communication and cooperation with the other hinge 62'. It is suitable for the first and second secondary sections 66' and 66" to be provided with handles 67 on the ends opposite their hinged ends. The hinges 62, 62' enable pivotable adjustment of the first and second secondary sections 66', 66" about the primary section 66 thus enabling an operator to fit the laser applicator 60 to a subject's body portion while they are lying in a prone position on a suitable support, and thereby provide excellent contact between each of the hinged sections 66, 66', 66" and the body portion regardless of the contours and extent of protuberations caused by excessive solid and semi-solid fat content in the underlying adipose cells. Consequently, the application of low-power laser irradiation to a subject's body portion by this embodiment of the laser applicator of the present invention will provide exceptional liquefaction of the solid and semi-solid fat content in the underlying adipose cells. Although FIG. 4 illustrates that the three hinged sections 66, 66', 66" are rectangular, is within the scope of the present invention to provide various suitable shapes such as circular, elliptical, sigmoidal, obround, gibbous and the like, that are hingedly interconnectable to enhance the comfort of a subject when the laser applicator 60 is contacting a portion of their body surface. Further more, it is suitable to provide a primary section 66 configured with a first shape e.g., rectangular, and secondary sections 66', 66" configured with one or more other types of shapes. The secondary sections may be symmetrically paired or alternatively, asymmetrically paired. It is to be understood that effective lipolysis treatments comprising liquefaction of solid and semi-solid fats in adipose cells may be provided by a laser applicator comprising a pair of hingedly interconnected sections, each section comprising at least a PCB, a contact plate, a laser diode, a framework, a suitable housing and cooperating hinge components. Alternatively, effective lipolysis treatments may be provided by a laser applicator comprising more than three hingedly interconnected and sections configured as described above. It is suitable to configure one of the sections, e.g. a primary section exemplified in FIG. 4, for engaging a vertically adjustable positioning device 68 communicating and cooperating with a vertical support 69, to enable able a subject to contact a selected body portion with the contact plates while in a standing position. Those skilled in these arts will understand that the vertically adjustable positioning device 68 may be optionally provided with a pivoting component (not shown) for enabling the rotation of the laser applicator from a horizontal plane to a vertical plane. It is also within the scope of the present invention to incorporate a laser control device components into the positioning device 68.

Figure 5:
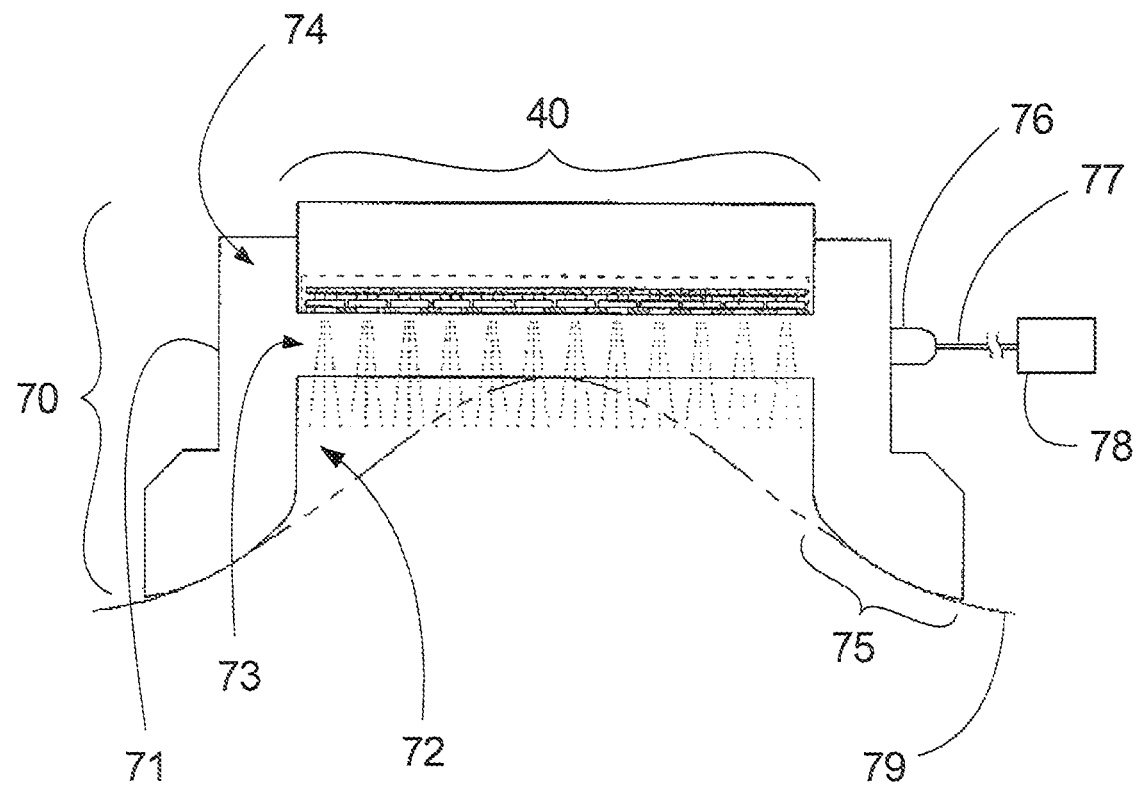
FIG. 5 is a cross-sectional schematic side view of another exemplary laser applicator system according to the present invention.

The present invention also provides devices configured to cooperate with laser applicators exemplified in FIGS. 1 and 2 to facilitate subcutaneous delivery of lipolysis treatments for liquefaction of solid and semi-solid fats in adipose cells. One such exemplary device is illustrated in FIG. 5 and is generally configured to cooperate with laser applicators such as those exemplified in FIGS. 1 and 2, for the application of negative suction forces to a portion of a body surface concurrent with laser irradiation of the subcutaneous region underlying the body surface. The vacuum suction device 70 comprises a molded cylindrical body 71 defining an inner bowl area 72 and is provided with a molded base 73 having an outward-extending receptacle 74 in the apex region of the molded body for receiving and sealably retaining therein a laser applicator 40 for example as exemplified in FIG. 2 and generally configured with housing into which are fitted a PCB, a contact plate, and a plurality of laser diodes each communicating with a transparent window or lens provided therefor in the contact plate. The molded base 73 of receptacle 74 is provided with ports configured to communicate with the contact plate's transparent windows or lens of the laser applicator 40 thereby providing irradiation routes for the laser light waves from the laser applicator 40 to the body surface portion 79 contained within the area defined by the rim 75 of the molded body 71. A vacuum port 76 communicating with the inner bowl area 72 is provided on the outer surface of the molded body 71. The vacuum port 76 is configured to sealing engage a vacuum line 77 interconnected to a vacuum pump 78.

An exemplary method for the use of the laser applicator 40 in combination with the suction device 70 illustrated in FIG. 5, comprises sealably installing the laser applicator 40 into the receptacle 74 in the base of the molded bowl 72, then interconnecting the laser applicator 40 to a suitable control device (not shown) comprising at least a power supply device, circuitry interconnecting software-controllable electronic devices configured for at least one of generating, transmitting, recording, processing, storing and reporting electronic signals useful for manipulable modulation of the output from the power supply device for generation of laser light waves. The suction device 70 is then placed onto a subject's body surface portion targeted to receive the lipolysis treatment so that the entire rim 75 surface is in contact with the subject's skin. The vacuum pump 78 is then engaged thereby applying a suction force through the vacuum line 77 and vacuum port 76 to the inner bowl area 72. The suction force draws the subject's body surface toward the base area 73 of the molded bowl 72 so that it is in close proximity to the laser diodes of the laser applicator 40. The laser control device is then manipulably operated to generate selected amounts of laser energy from the range of 10 mW to 100 mW by the laser diodes 15 for irradiation of the body portion that is drawn by the suction force within the inner bowl area 72. The laser irradiation penetrates into the subcutaneous region of drawn-in body portion and liquefies solid and semi-solid fats in the adipose cells therein. The suction force exerted on the body portion facilitates the movement of the liquefied fat from the adipose cells into the interstitial spaces from where it is absorbed into the lymphatic system and removed from the body portion by the subject's normal physiological processes.

Figure 6:
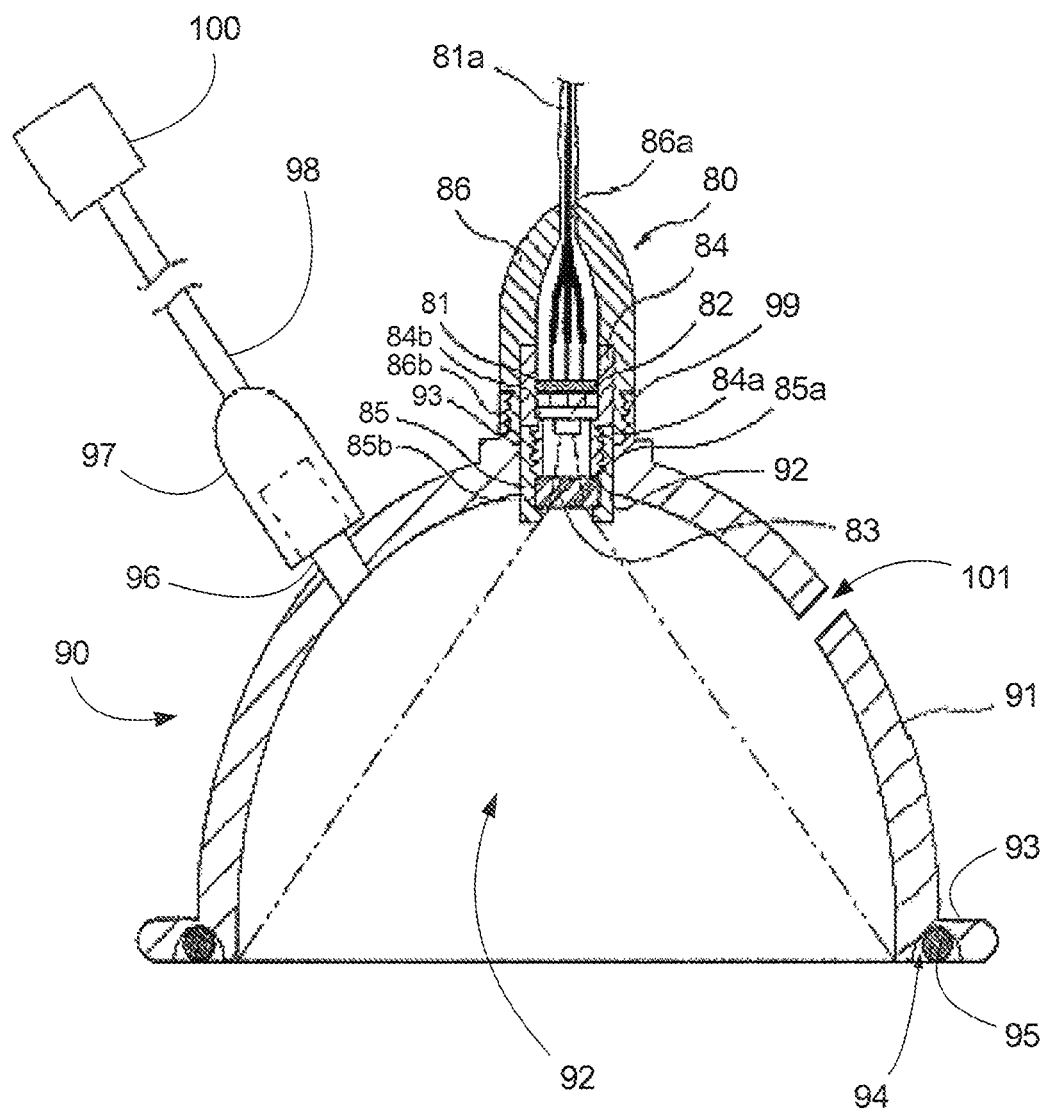
FIG. 6 is a cross-sectional side view of another exemplary embodiment of a laser applicator system according to the present invention.
Figure 7:
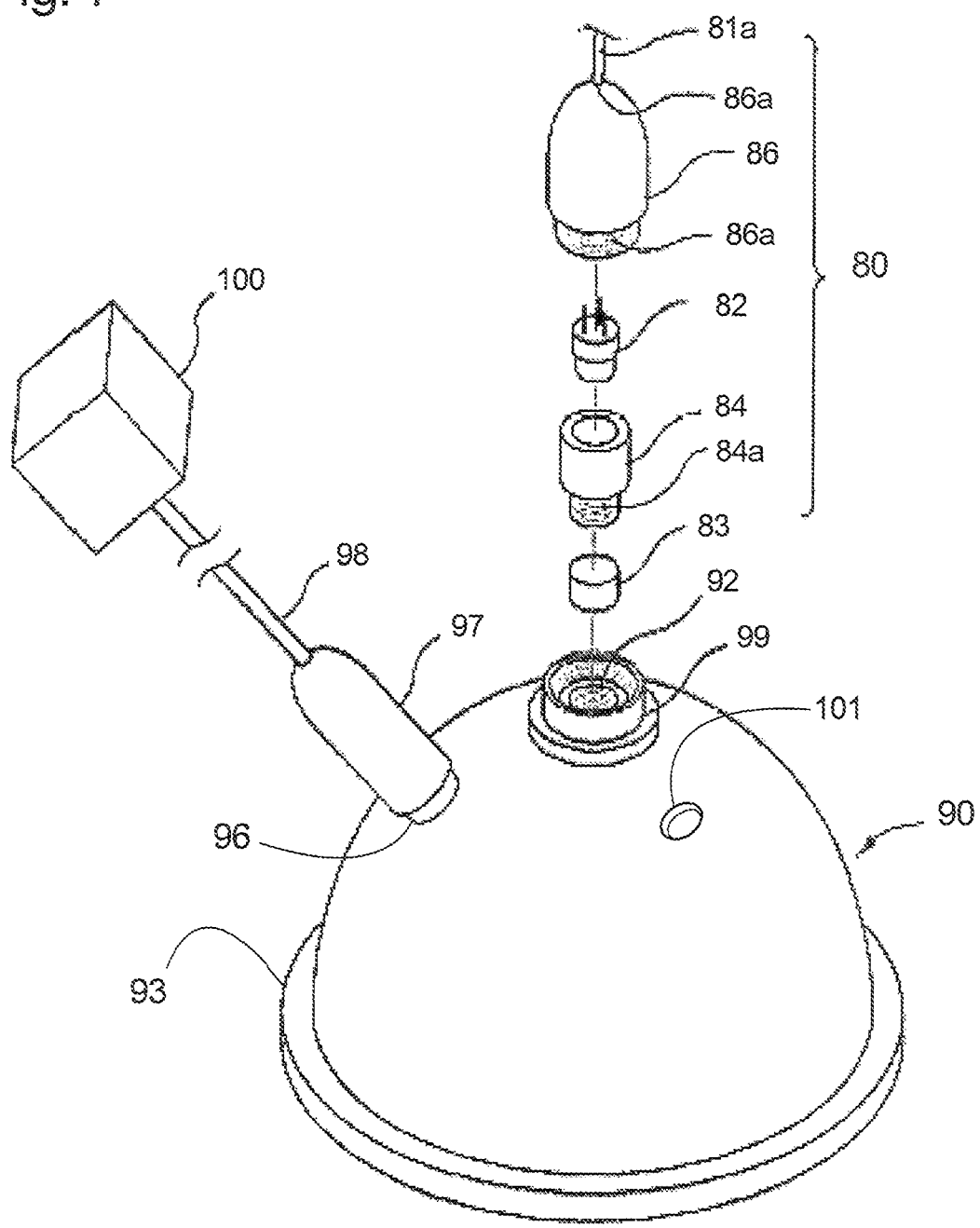
FIG. 7 is an exploded perspective view of the embodiment shown in FIG. 6.

Another exemplary laser applicator system according to the present invention is illustrated in FIGS. 6 and 7 and generally comprises a molded bowl-shaped suction device 90 configured to releasably engage and cooperate with a low-power generating laser module 80. The laser-generating module 80 generally comprises a PCB 81 configured for receiving power, a low level light-emitting laser diode 82 with a power output in the range comprising about 10 mW to about 100 mW with light waves in the range of 635 nm to 680 nm electrically connected to the PCB 81, a transparent window or lens 83 disposed adjacent to the laser diode 82, upper and lower fixtures 84 and 85 for accommodating the PCB 81, the laser diode 82, and the transparent window or lens 83, which are detachable from each other, and a cover 86 installed outside the upper and lower fixtures 84 and 85. A male-threaded part 84a and a female-threaded part 85a are provided at a lower periphery of the upper fixture 84 and an upper periphery of the lower fixture 85 to be threadedly engaged with each other, a hooking threshold 84b is formed at an inner periphery of the upper fixture 84 to be engaged with the PCB 81, and a groove 85b is formed at a lower periphery of the lower fixture 85 to be engaged with the transparent window or lens 83. A selected interval between the laser diode 82 and the transparent window or lens 83 can be controllably provided by progressively engaging or disengaging the male threaded part 84a and the female threaded part 85a formed at the upper and lower fixtures 84 and 85. The PCB 81 is connectable to a cable 81a to receive power, and an insertion hole 86a for inserting the cable 81a therethrough, is provided at an upper part of the cover 86.

The bowl-shaped suction device 90 comprises a body 91 provided with a continuous outer rim having a molded lip 93. The outward-extending surface portion of the molded lip 93 may be optionally provided with a continuous channel 94 configured to receive and cooperate with a ring 95 comprising a suitable resilient material. Alternatively, the continuous channel 94 may be configured to receive and cooperate with a plurality of balls (not shown). A vacuum port 97 communicating with the inner bowl area 92 with line 96 is provided on the outer surface of the molded body 91. The vacuum port 92 is configured to sealing engage a vacuum line 98 interconnected to a vacuum pump 100. An upward extending coupler portion 99 is provided at the apex of the body 91, with a bore therethrough the molded body 91 for receiving and sealingly engaging the laser module 80. In order to sealably engage the suction device 90 and the laser-generating module 80, female and male threaded parts 83 and 86b are formed about the inner upper section of the bore extending through the upper section of the coupler portion 99 and an outer periphery of the cover 86. Further, the upper and lower fixtures 84 and 85 may be formed of a thermal interface material for radiating heat generated from the laser diode 82 of the laser-generating module 80. An interval between the laser diode 82 and the transparent window or lens 83 can be adjusted by first separating the cover 86 from the laser diode 82, then controllably engaging or disengaging the male threaded part 84a and the female threaded part 85a formed at the upper and lower fixtures 84 and 85.

An exemplary method for the use of the laser applicator 80 in combination with the suction device 90 illustrated in FIGS. 6 and 7, comprises sealably installing the laser-generating module 80 into the coupler 99 at the apex of the molded body 91, then interconnecting the laser generating module 80 to a suitable control device (not shown) comprising at least a power supply device, circuitry interconnecting software-controllable electronic devices configured for at least one of generating, transmitting, recording, processing, storing and reporting electronic signals useful for manipulable modulation of the output from the power supply device for generation of laser light waves. The suction device 90 is then placed onto a subject's body surface portion targeted to receive the lipolysis treatment so that the outward-facing surface of the molded lip 93 is in contact with the subject's skin. The vacuum pump is then engaged thereby applying a suction force through the vacuum line 96 and vacuum port 97 to the inner bowl area 92. The suction force draws the subject's body surface toward the base area of the molded bowl 91 so that it is in close proximity to the laser diode 82 of the laser-generating module 80. The laser control device is then manipulably operated to generate selected amounts of laser energy from the range of 10 mW to 100 mW by the laser diode 82 for irradiation of the body portion that is drawn by the suction force within the inner bowl area 92. The laser irradiation penetrates into the subcutaneous region of drawn-in body portion and liquefies solid and semi-solid fats in the adipose cells therein. The suction force exerted on the body portion facilitates the movement of the liquefied fat from the adipose cells into the interstitial spaces from where it is absorbed into the lymphatic system and removed from the body portion by the subject's normal physiological processes. It is suitable for an operator to manipulate the vacuum suction device 90 while it is cooperating with the laser-generating module 80, about a subject's body surface working toward the groin area and/or the armpit areas, where those skilled in these arts know that a great abundance of lymphatic vessels are situated, thereby enhancing removal of the liquefied fats from the interstitial areas receiving the lipolysis treatments as described herein.

At least one optional pressure-release aperture 101 may be provided therethrough the molded body 91 to enable an operator to exert manipulable manual control of the partial release of the suction force generated by the suction device 90 during operation, by engaging and disengaging one of their fingers with the pressure-release aperture 101. The shape of the pressure-release aperture 101 may be circular, oval, rectangular and suitably sized. The pressure-release aperture 101 enables an operator to position the suction device 90 with a target portion of a subject's body surface, then engage the vacuum pump 100 and the and the laser control device and finally engage one of their fingers with the pressure-release aperture 101 thereby applying a suction force to the target portion of the subject's body surface. The operator may then easily move the vacuum suction device 90 to another target portion of the subject's body surface by partially releasing the suction force from within the suction device 90 by removing their finger from the pressure-release aperture 101, then sliding the vacuum suction device 90 along the subject's body surface to the next target portion, and then re-applying the suction force by re-engaging their finger with the pressure-release aperture 101. Those skilled in these arts will understand that the an operator may affect and control the movement of liquefied fat from within the adipose cells into the interstitial spaces, and then about the subcutaneous region underlying the body surface by controllably applying and releasing by engaging and disengaging their finger with the pressure-release aperture 101, the suction force generated within vacuum suction device 90 while controllably moving the vacuum suction device 90 about the subject's body surface. For example, using this method as described, the liquefied fat may be thus manipulably moved from a subject's target body portions to their groin area ore alternatively to an armpit, where lymphatic vessels are abundant and will thereby remove the liquefied fat via the subject's physiological processes.

Figure 8:
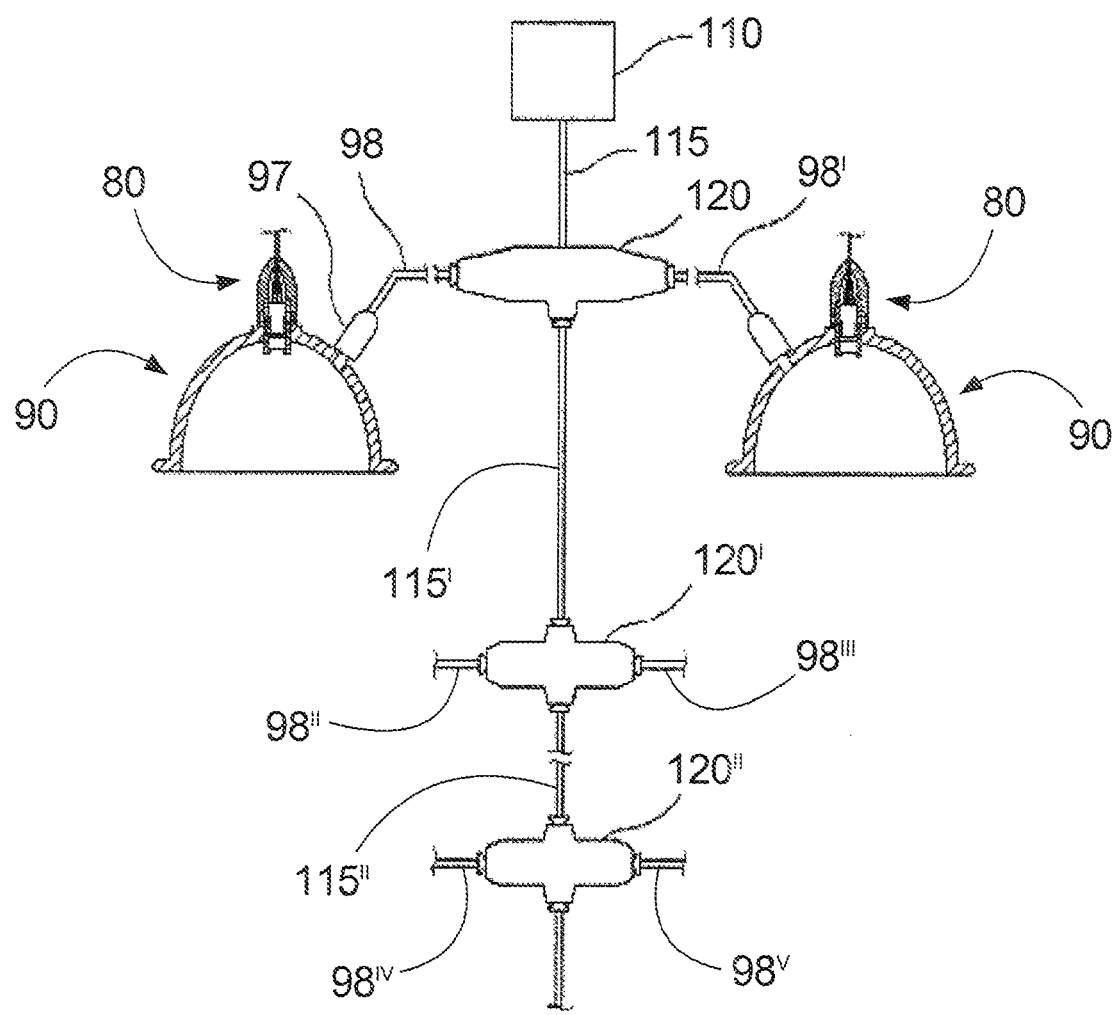
FIG. 8 is a schematic diagram of an exemplary expanded laser application system according to the present invention, comprising a plurality of cooperating embodiments exemplified in FIGS. 6 and 7.

It is also within the scope of the present invention as exemplified in FIG. 8 to provide one or more relays 120 communicating with a vacuum pump 110 via vacuum line 115, and further interconnected and cooperating with two or more laser applicator systems as exemplified in FIGS. 6 and 7. For example, a suitable exemplary configuration comprises two laser applicator systems interconnected by a single relay to one vacuum pump and a laser control device. This configuration makes it possible for an operator to controllably and manipulably provide lipolysis treatments to a subject using two laser applicators of the present invention. Another suitable exemplary configuration is providing additional vacuum lines 115', 115" communicating with a plurality of relays 120', 120" interconnected with two or more subject treatment rooms with vacuum lines 98", 98''', 98'''', 98$^V$, each containing at least one laser applicator system and a control device of the present invention. This configuration makes it possible for two or more operators to provide concurrently lipolysis treatments to multiple subjects, using the laser application systems of the present invention interconnected and cooperating with one central vacuum pump.

Figure 9:
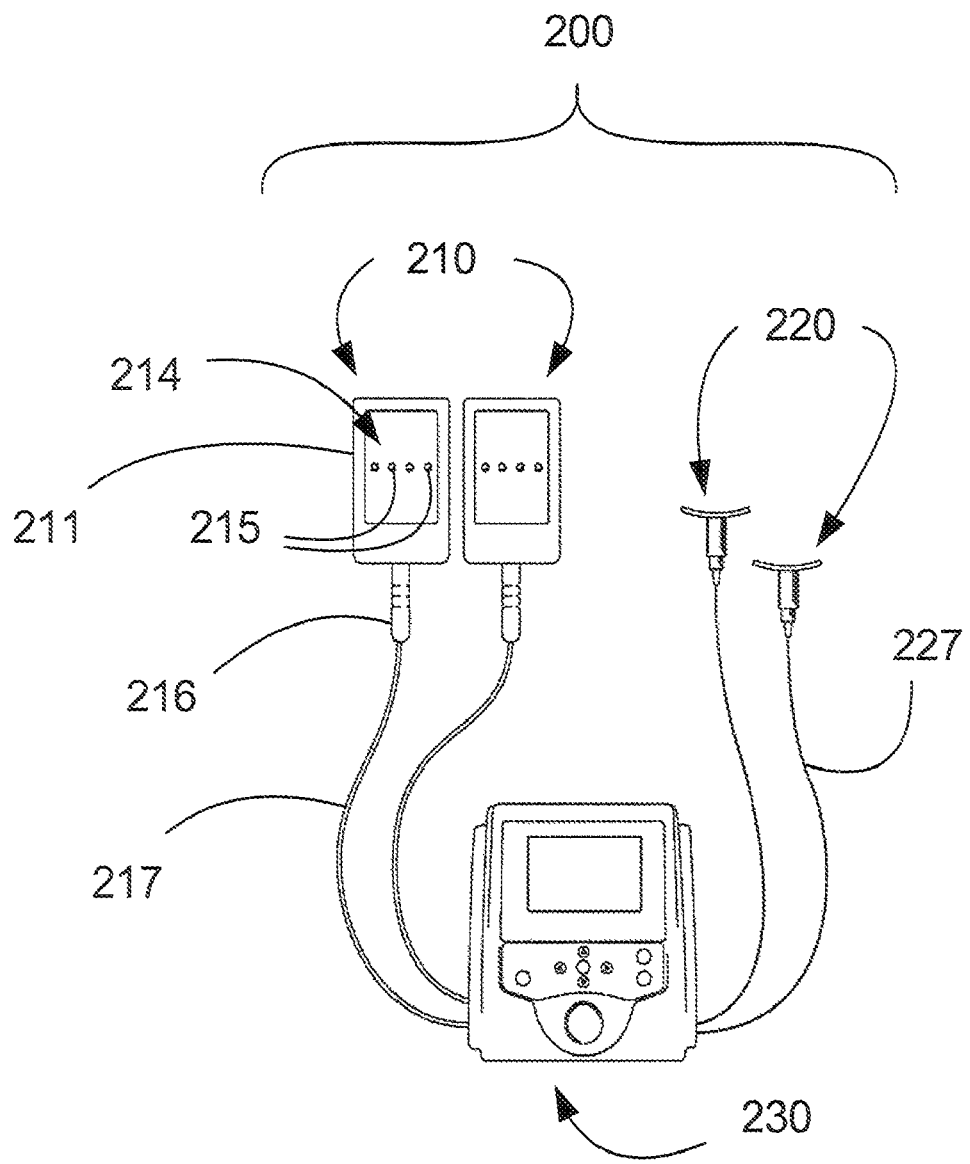
FIG. 9 is a schematic view of an exemplary lipolysis system provided with a plurality of two types of laser applicators according to the present invention.

Another exemplary laser applicator system according to the present invention is illustrated in FIGS. 9 and 10 and generally comprises at least one first laser applicator 210 provided with a plurality of low-power laser diodes, at least one second laser applicator 220 provided with one laser diode, and a laser control device 230 configured for controllably communicating and cooperating with the laser applicators 210, 220. The first laser applicator generally comprises a housing 211 configured to contain and retain a contact plate 14 fitted and cooperating with a plurality of laser diodes 215. The contact plate 214 is configured to contact a portion of a subject's body surface. Suitable laser diodes are exemplified by multi-channel AlGaLnP laser diodes configured for continuous and modulated continuous power outputs in the range of about 130 mW to about 170 mW of light waves in the range of about 630 nm to about 680 nm with a modulation frequency of 0 to about 10 Hz. It is suitable for the first laser applicator 210 to be hardwired-connected to the laser control device 230. Alternatively, the first laser applicator 210 may be provided with a female electrical receptacle (not shown) configured for releasably engaging male plug lead 216 connected to the laser control device 230 by a suitable gauge wire 217. The second laser applicator 220 is configured to cooperate and communicate with one suitable laser diode. As exemplified in FIG. 10, the second laser applicator comprises a housing 221 having a generally elongate concave surface 222 configured for contacting a subject's body surface with a laser diode receptacle 223 extending away from the concave surface 222 of the housing 221. An aperture 224 communicating with the laser diode receptacle is provided about center of the concave surface for transmitting laser light therethrough. A suitable laser diode for the second laser applicator is exemplified by a multi-channel AlGaLnP laser diode configured for continuous and modulated continuous power outputs in the range of about 0 mW to about 50 mW of light waves in the range of about 630 nm to about 680 nm with a modulation frequency of 0 to about 10 Hz. It is suitable for the second laser applicator 220 to be connected to the laser control device 230 with a suitable gauge wire 227. The laser control device 230 comprises a graphical user interface (GUI), a visual display unit 231, suitable user input electronic devices 232 configured for communicating and cooperating with power modulation hardware, and suitably configured software. Although reference is made herein to interconnecting the exemplary laser applicators 210 and 220 with the exemplary laser control device with wires 217, 227, it is within the scope of the present invention to configure the laser applicators 210, 220 and the laser control device 230 with provide wireless transmission/reception devices for cooperatively controllably generating laser light waves and energy for application of lipolysis treatments to a subject's body surface.

Figure 11:
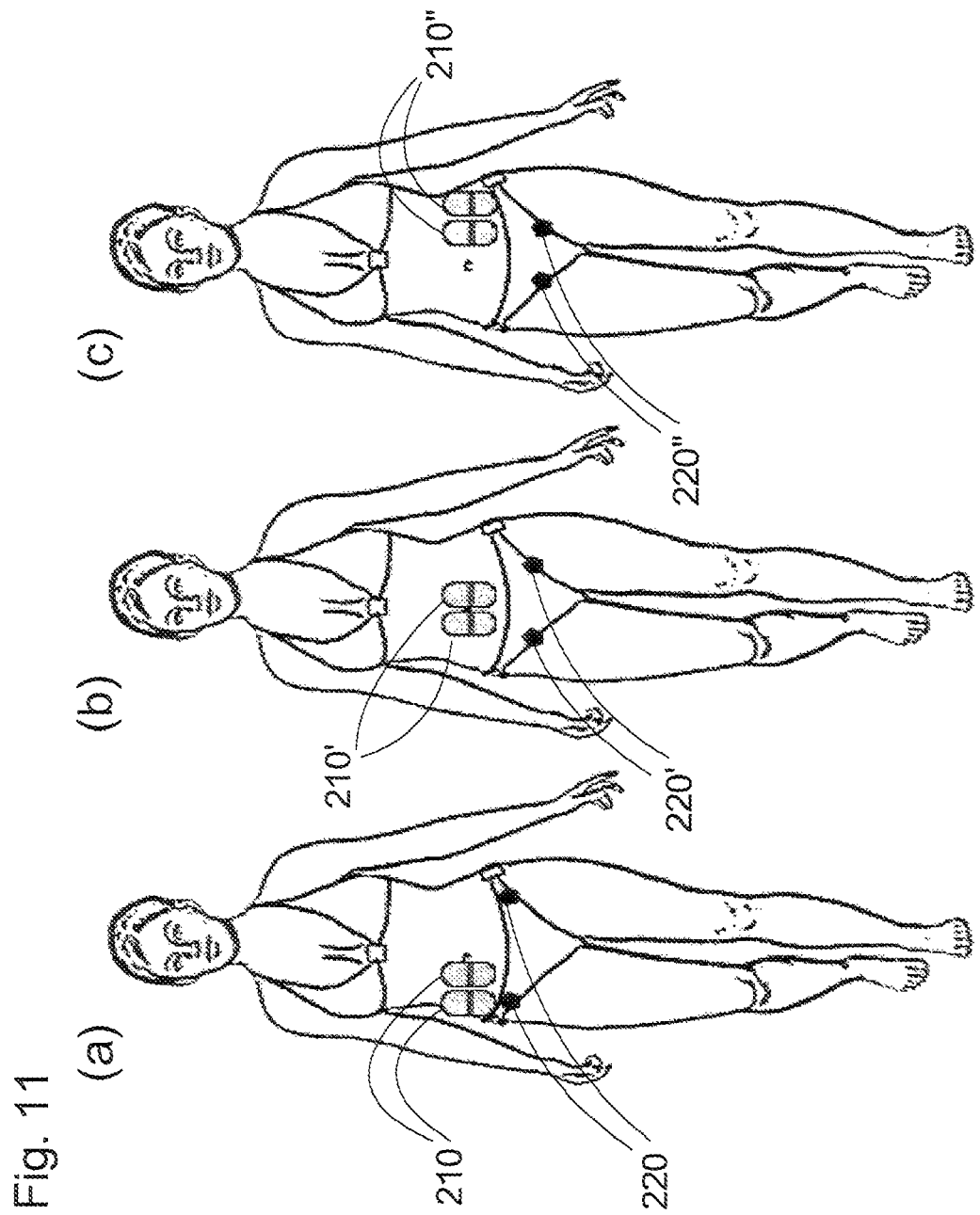
FIGS. 11(a)-11(c) are schematic illustrations of exemplary positioning of the laser applicators of the lipolysis system shown in FIG. 9, about a subject's body torso for liquefaction of fats about their waistline.

Exemplary methods for the use of the laser applicators in cooperation with the laser control devices of the lipolysis systems of the present invention are illustrated in FIGS. 11-15. For example, a suitable method for liquefaction of subcutaneous fats about a subject's waistline and for concurrent removal of the liquefied fats from that area of the of the subject's body is illustrated in FIG. 11. As shown in FIG. 11(a), at least two first laser applicators 210 are first positioned next to each other on the right side of the subject's body about the right lateral waistline and secured in place with a suitable device (not shown) as exemplified by adhesive strips, elastic band, adjustable belt, adjustable strap and the like. At least one second laser applicator 220 is positioned approximate the upper inguinal joint area defining the connection of each upper thigh with the body torso after which both laser applicators 220 are secured in place with a suitable device as exemplified by adhesive strips, elastic bands and the like. The laser control device (not shown in FIG. 11) is then manipulated to provide about 10 to about 30 minutes of a first laser irradiation to the body surfaces contacting the laser applicators 210, 220 and the underlying subcutaneous regions for liquefaction of fats in adipose cells therein. At the conclusion of the first laser irradiation period, the at least two first laser applicators are moved to a second position about the medial waistline in the middle of the subject's torso shown as 210' in FIG. 11(b) and then secured in place. Each second laser applicator is moved downward along the inguinal joint area defining the connection of each upper thigh with the body torso to about the mid-point of the joint area shown as 220' in FIG. 11(b) and then is secured in place. The laser control device is then manipulated to provide about 10 to about 30 minutes of a second laser irradiation to the body surfaces contacting the laser applicators in the 210'and 220' positions and the underlying subcutaneous regions for liquefaction of fats in adipose cells therein. At the conclusion of the second laser irradiation period at least two first laser applicators are moved to a third position about the left lateral waistline of the subject's torso as shown as 210" in FIG. 11(c) and then secured in place. Each second laser applicator is moved downward along the inguinal joint area defining the connection of each upper thigh with the body torso to about the lower end of the inguinal joint area shown as 220" in FIG. 11(c) and then is secured in place. The laser control device is then manipulated to provide about 10 to about 30 minutes of a third laser irradiation to the body surfaces contacting the laser applicators in the 210"and 220" positions and the underlying subcutaneous regions for liquefaction of fats in adipose cells therein. At the conclusion of the third laser irradiation period the first and second laser applicators are removed and if so desired, employed for further lipolysis treatments elsewhere on the subject's body surface. It is to be noted that laser irradiation provided by the second laser applicators 220 positioned about the inguinal joint areas will stimulate the lymph glands and associated lymph vessels located in the subcutaneous areas of the inguinal joint areas and thus facilitate movement of liquefied fat from the subcutaneous regions underlying the portions of the body surface receiving laser irradiation from the first laser applicators 210, will facilitate its movement to the lymph glands and its subsequent removal from those areas by the lymphatic system.

Figure 12:
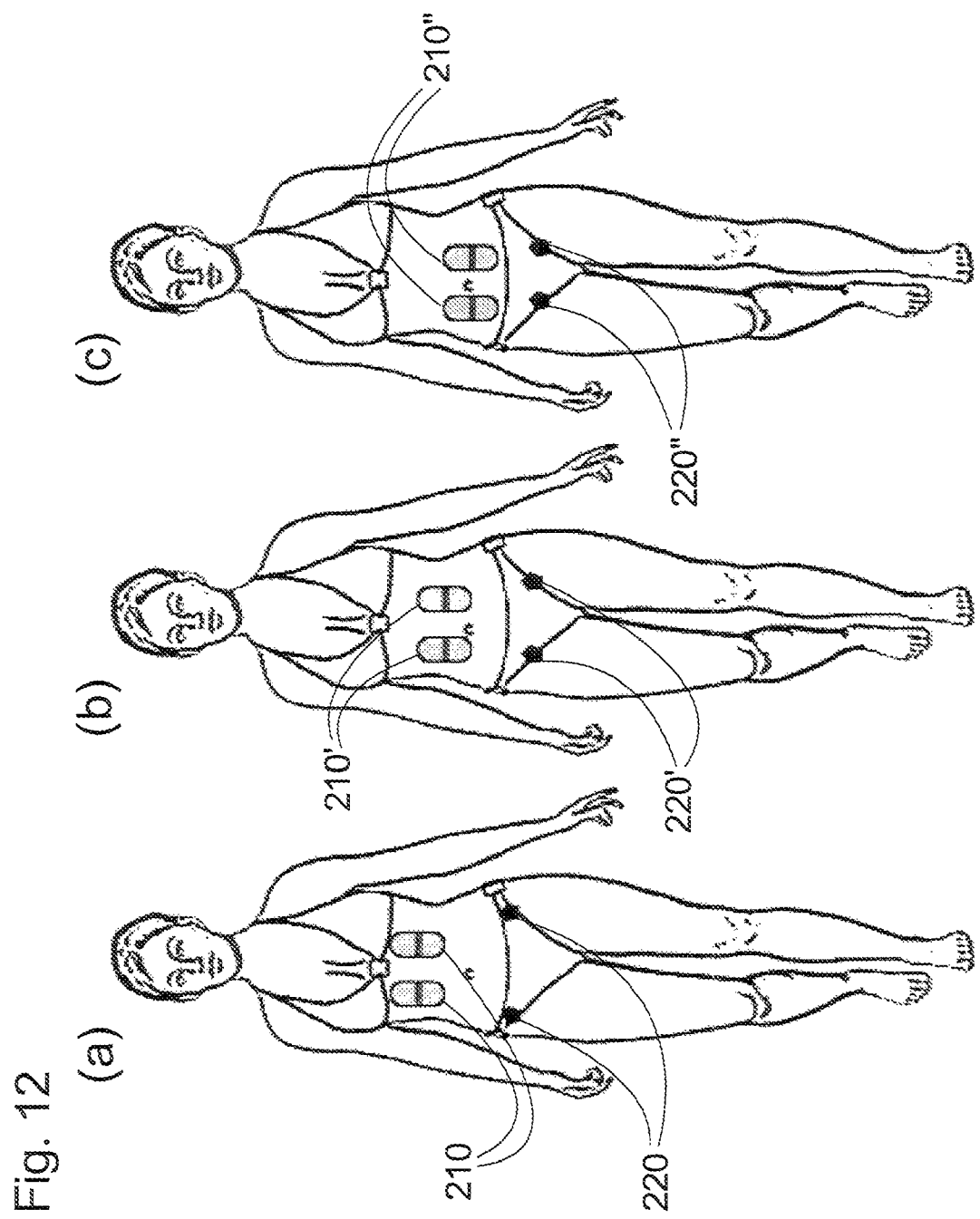
FIGS. 12(a)-12(c) are schematic illustrations of exemplary positioning of the laser applicators about a subject's body torso for liquefaction of fats about their abdominal oblique muscle areas.

FIGS. 12(a)-12(c) are schematic illustrations of exemplary positioning of the laser applicators about a subject's body torso for liquefaction of fats about their abdominal oblique muscle areas. As shown in FIG. 12(a), at least two first laser applicators 210 are first positioned next to each other about the upper lateral oblique area of the subject's body torso and secured in place with a suitable device (not shown) as exemplified by adhesive strips, elastic band, adjustable belt, adjustable strap and the like. At least one second laser applicator 220 is positioned approximate the upper inguinal joint area defining the connection of each upper thigh with the body torso after which both laser applicators 220 are secured in place with a suitable device as exemplified by adhesive strips, elastic bands and the like. The laser control device (not shown in FIG. 12) is then manipulated to provide about 10 to about 30 minutes of a first laser irradiation to the body surfaces contacting the laser applicators 210, 220 and the underlying subcutaneous regions for liquefaction of fats in adipose cells therein. At the conclusion of the first laser irradiation period, the at least two first laser applicators are moved to a second position about the middle oblique area of the subject's body torso shown as 210' in FIG. 12(b) and then secured in place. Each second laser applicator is moved downward along the inguinal joint area defining the connection of each upper thigh with the body torso to about the mid-point of the joint area shown as 220' in FIG. 12(b) and then is secured in place. The laser control device is then manipulated to provide about 10 to about 30 minutes of a second laser irradiation to the body surfaces contacting the laser applicators in the 210'and 220' positions and the underlying subcutaneous regions for liquefaction of fats in adipose cells therein. At the conclusion of the second laser irradiation period at least two first laser applicators are moved to a third position about the lower oblique area of the subject's torso as shown as 210" in FIG. 12(c) and then secured in place. Each second laser applicator is moved downward along the inguinal joint area defining the connection of each upper thigh with the body torso to about the lower end of the inguinal joint area shown as 220" in FIG. 12(c) and then is secured in place. The laser control device is then manipulated to provide about 10 to about 30 minutes of a third laser irradiation to the body surfaces contacting the laser applicators in the 210"and 220" positions and the underlying subcutaneous regions for liquefaction of fats in adipose cells therein. At the conclusion of the third laser irradiation period the first and second laser applicators are removed and if so desired, employed for further lipolysis treatments elsewhere on the subject's body surface. It is to be noted that laser irradiation provided by the second laser applicators 220 positioned about the inguinal joint areas will stimulate the lymph glands and associated lymph vessels located in the subcutaneous areas of the inguinal joint areas and thus facilitate movement of liquefied fat from the subcutaneous regions underlying the portions of the body surface receiving laser irradiation from the first laser applicators 210, will facilitate its movement to the lymph glands and its subsequent removal from those areas by the lymphatic system.

Figure 13:
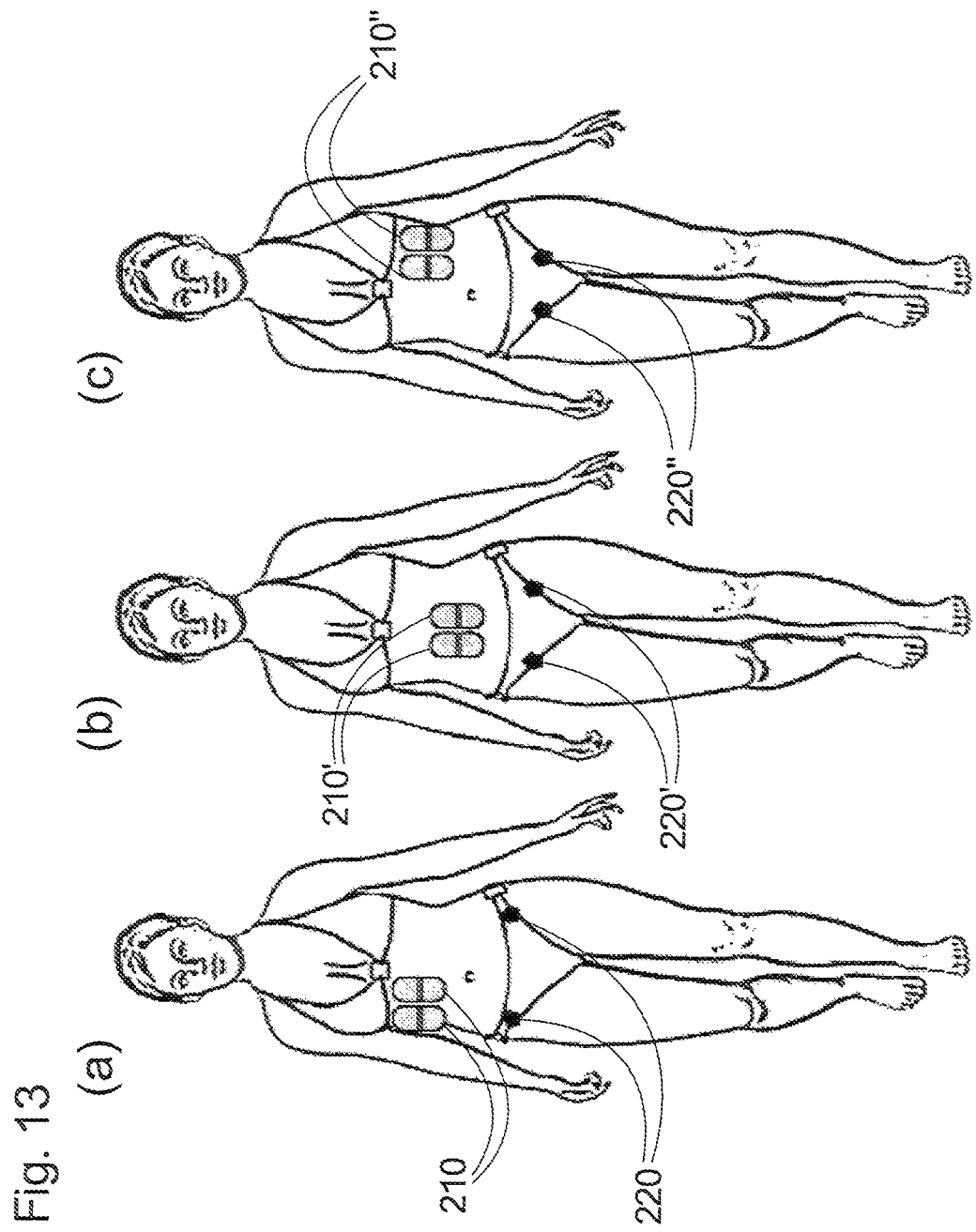
FIGS. 13(a)-13(c) are schematic illustrations of exemplary positioning of the laser applicators about a subject's body torso for liquefaction of fats about their upper abdominal areas.

FIGS. 13(a)-13(c) are schematic illustrations of exemplary positioning of the laser applicators about a subject's body torso for liquefaction of fats about their upper abdominal areas. As shown in FIG. 13(a), at least two first laser applicators 210 are first positioned next to each other about the upper abdomen area on the right side of the subject's body and secured in place with a suitable device (not shown) as exemplified by adhesive strips, elastic band, adjustable belt, adjustable strap and the like. At least one second laser applicator 220 is positioned approximate the upper inguinal joint area defining the connection of each upper thigh with the body torso after which both laser applicators 220 are secured in place with a suitable device as exemplified by adhesive strips, elastic bands and the like. The laser control device (not shown in FIG. 13) is then manipulated to provide about 10 to about 30 minutes of a first laser irradiation to the body surfaces contacting the laser applicators 210, 220 and the underlying subcutaneous regions for liquefaction of fats in adipose cells therein. At the conclusion of the first laser irradiation period, the at least two first laser applicators are moved to a second position about the middle upper abdomen area of the subject's body torso shown as 210' in FIG. 13(b) and then secured in place. Each second laser applicator is moved downward along the inguinal joint area defining the connection of each upper thigh with the body torso to about the mid-point of the joint area shown as 220' in FIG. 13(b) and then is secured in place. The laser control device is then manipulated to provide about 10 to about 30 minutes of a second laser irradiation to the body surfaces contacting the laser applicators in the 210'and 220' positions and the underlying subcutaneous regions for liquefaction of fats in adipose cells therein. At the conclusion of the second laser irradiation period at least two first laser applicators are moved to a third position about the upper abdomen area on the right side of the subject's body as shown as 210" in FIG. 13(c) and then secured in place. Each second laser applicator is moved downward along the inguinal joint area defining the connection of each upper thigh with the body torso to about the lower end of the inguinal joint area shown as 220" in FIG. 13(c) and then is secured in place. The laser control device is then manipulated to provide about 10 to about 30 minutes of a third laser irradiation to the body surfaces contacting the laser applicators in the 210"and 220" positions and the underlying subcutaneous regions for liquefaction of fats in adipose cells therein. At the conclusion of the third laser irradiation period the first and second laser applicators are removed and if so desired, employed for further lipolysis treatments elsewhere on the subject's body surface.

Figure 14:
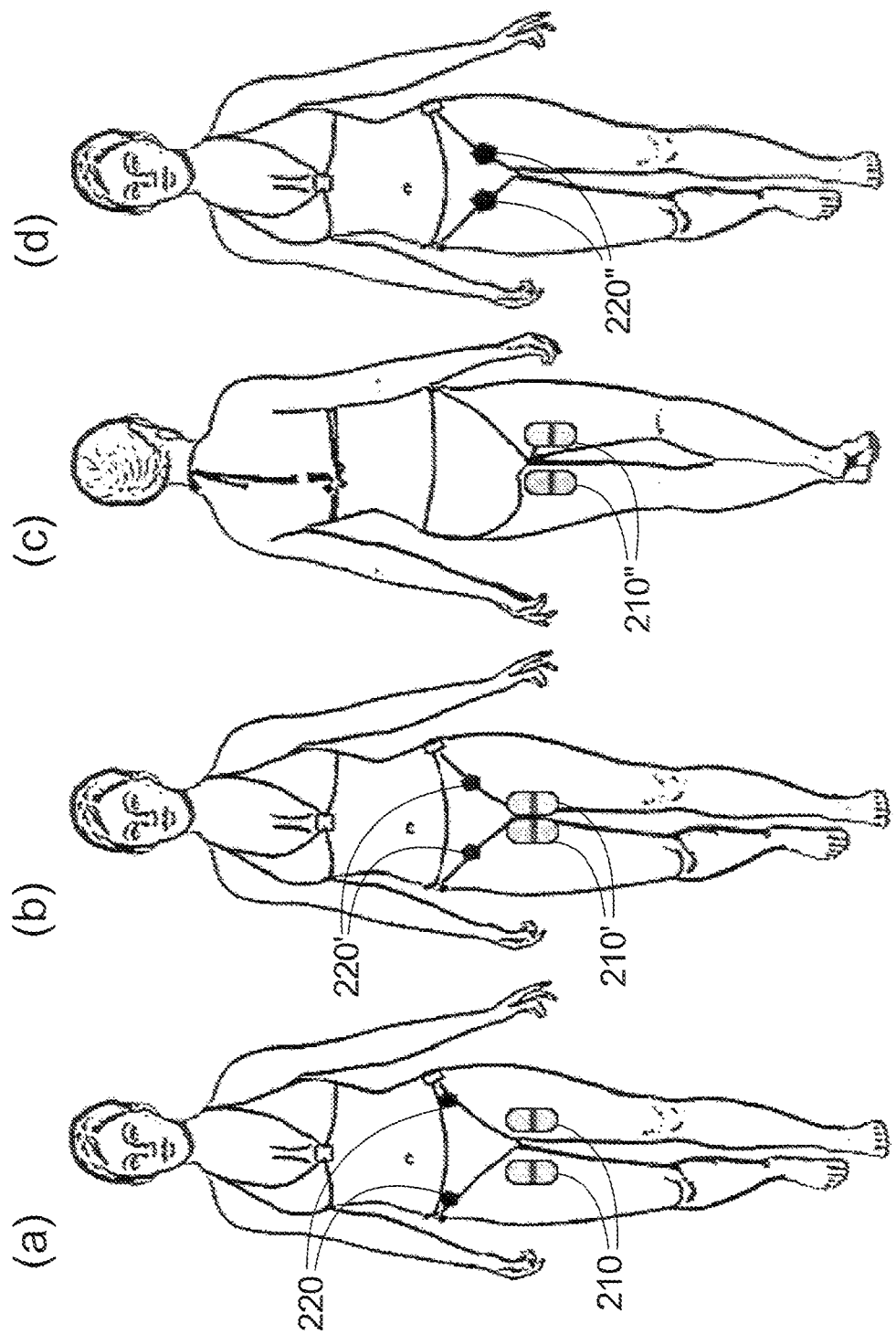
FIGS. 14(a)-14(d) are schematic illustrations of exemplary positioning of the laser applicators about a subject's body torso for liquefaction of fats about their upper thigh areas.

FIGS. 14(a)-14(d) are schematic illustrations of exemplary positioning of the laser applicators about a subject's body torso for liquefaction of fats about their upper thigh areas. As shown in FIG. 14(a), one first laser applicator 210 is positioned on the subject's right upper thigh adjacent a vertical linear axis extending upward from the right knee while a second first applicator 210 is positioned on the subject's left upper thigh adjacent a vertical linear axis extending upward from the left knee. Both first laser applicators are secured in place with a suitable device (not shown) as exemplified by adhesive strips, elastic band, adjustable belt, adjustable strap and the like. At least one second laser applicator 220 is positioned approximate the mid-portion area of the inguinal joint area defining the connection of each upper thigh with the body torso as shown in FIG. 14(d) after which both laser applicators 220 are secured in place with a suitable device as exemplified by adhesive strips, elastic bands and the like. The laser control device (not shown in FIG. 14) is then manipulated to provide about 10 to about 30 minutes of a first laser irradiation to the body surfaces contacting the laser applicators 210, 220 and the underlying subcutaneous regions for liquefaction of fats in adipose cells therein. At the conclusion of the first laser irradiation period, the first laser applicator 210 is re-positioned on the subject's right upper thigh to a position facing the left upper thigh while the second first applicator 210 is re-positioned on the subject's left upper thigh adjacent to a position facing the right upper thigh as shown in FIG. 14(b), and both are secured in place. The two second laser applicators are maintained in the same position shown in FIG. 14(d). The laser control device is then manipulated to provide about 10 to about 30 minutes of a second laser irradiation to the body surfaces contacting the laser applicators in the 210'and 220' positions and the underlying subcutaneous regions for liquefaction of fats in adipose cells therein. At the conclusion of the second laser irradiation period, the first laser applicator 210 is re-positioned on the subject's right upper thigh to a backward-facing position while the second first applicator 210 is re-positioned on the subject's left upper thigh to a similar backward-facing position as shown in FIG. 14(c), and both are secured in place. The two second laser applicators are maintained in the same position shown in FIG. 14(d). The laser control device is then manipulated to provide about 10 to about 30 minutes of a third laser irradiation to the body surfaces contacting the laser applicators in the 210"and 220" positions and the underlying subcutaneous regions for liquefaction of fats in adipose cells therein. At the conclusion of the third laser irradiation period the first and second laser applicators are removed and if so desired, employed for further lipolysis treatments elsewhere on the subject's body surface.

Figure 15:
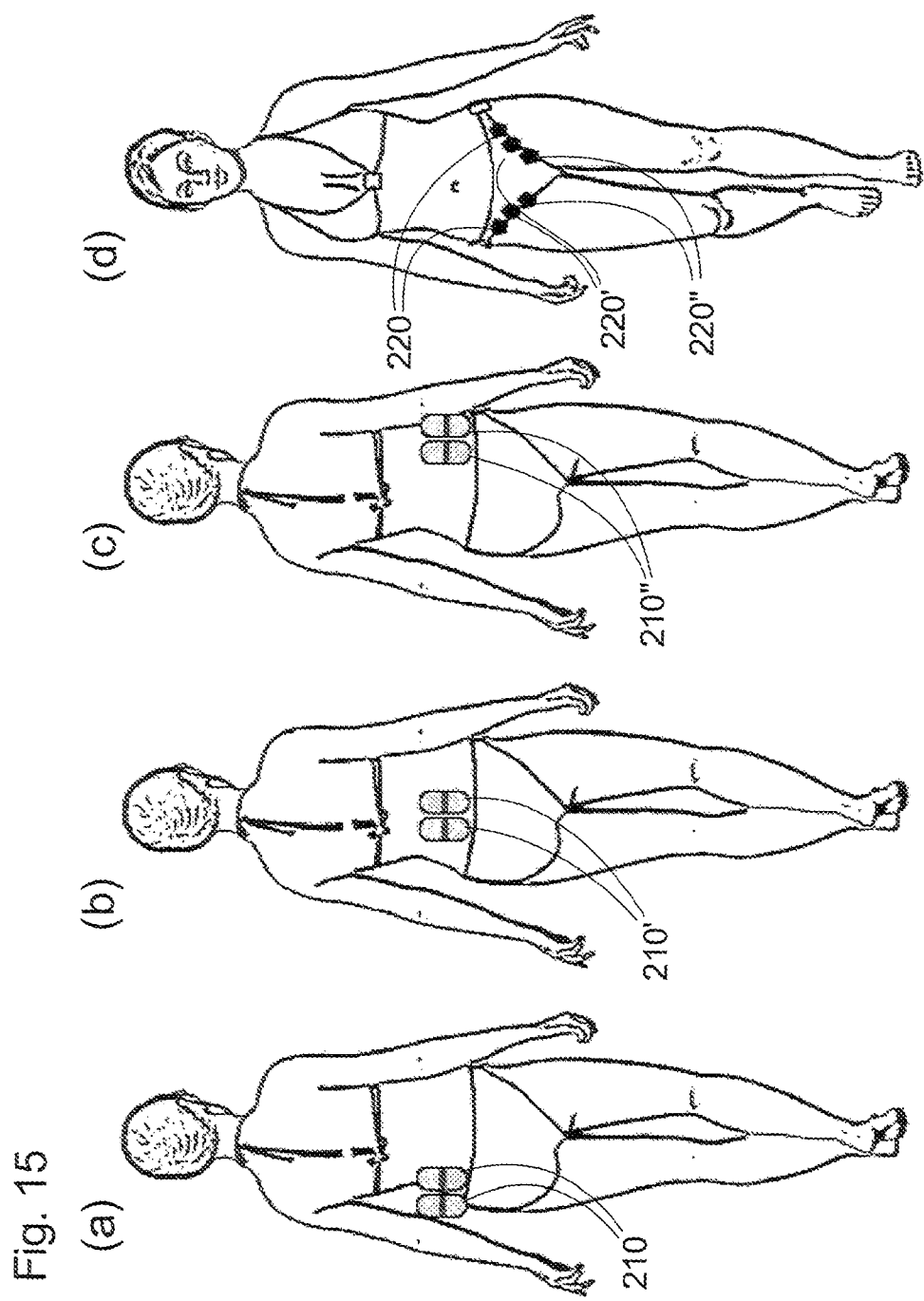
FIGS. 15(a)-15(d) are schematic illustrations of exemplary positioning of the laser applicators about a subject's body torso for liquefaction of fats about their lower back areas.

FIGS. 15(a)-15(d) are schematic illustrations of exemplary positioning of the laser applicators about a subject's body torso for liquefaction of fats about their lower back areas. As shown in FIG. 15(a), at least two first laser applicators 210 are first positioned next to each other on the left side of the subject's body about the hip area and secured in place with a suitable device (not shown) as exemplified by adhesive strips, elastic band, adjustable belt, adjustable strap and the like. At least one second laser applicator 220 is positioned approximate the upper inguinal joint area defining the connection of each upper thigh with the body torso as shown in FIG. 15(d) after which both laser applicators 220 are secured in place with a suitable device as exemplified by adhesive strips, elastic bands and the like. The laser control device (not shown in FIG. 15) is then manipulated to provide about 10 to about 30 minutes of a first laser irradiation to the body surfaces contacting the laser applicators 210, 220 and the underlying subcutaneous regions for liquefaction of fats in adipose cells therein. At the conclusion of the first laser irradiation period, the at least two first laser applicators are moved to a second position about the above the hip area in the middle of the subject's torso shown as 210' in FIG. 15(b) and then secured in place. Each second laser applicator is moved downward along the inguinal joint area defining the connection of each upper thigh with the body torso to about the mid-point of the joint area shown as 220' in FIG. 15(d) and then is secured in place. The laser control device is then manipulated to provide about 10 to about 30 minutes of a second laser irradiation to the body surfaces contacting the laser applicators in the 210'and 220' positions and the underlying subcutaneous regions for liquefaction of fats in adipose cells therein. At the conclusion of the second laser irradiation period at least two first laser applicators are moved to a third position about on the right side of the subject's body about the hip area as shown as 210" in FIG. 15(c) and then secured in place. Each second laser applicator is moved downward along the inguinal joint area defining the connection of each upper thigh with the body torso to about the lower end of the inguinal joint area shown as 220" in FIG. 15(d) and then is secured in place. The laser control device is then manipulated to provide about 10 to about 30 minutes of a third laser irradiation to the body surfaces contacting the laser applicators in the 210″ and 220″ positions and the underlying subcutaneous regions for liquefaction of fats in adipose cells therein. At the conclusion of the third laser irradiation period the first and second laser applicators are removed and if so desired, employed for further lipolysis treatments elsewhere on the subject's body surface.

Those skilled in these arts will understand that the exemplary methods shown in FIGS. 11-15 for the use of lipolysis systems to apply lipolysis treatments to a subject's body surface may be suitably modified to personalize the methods to individual subjects. For example, the lipolysis treatments about a certain body portion e.g., such as the waist area and the lower back area, may be applied in the reverse order to that described. Also, the exemplary methods are applicable to all areas about a subject's body torso and their extremities. Also, a suitable duration of laser irradiation applied to each body portion may be selected based on a target amount of fat liquefaction desired for each target body portion. Furthermore, those skilled in these arts will understand that the laser applicators, the lipolysis systems and the methods for their use according to the present invention may be employed for body sculpting, contouring and toning by: (a) selection of the numbers of first and second laser applicators used for each lipolysis treatment, and (b) by selecting specific combinations of body torso and extremity target surface areas for each lipolysis treatment. For clarity, lipolysis treatment in this context means a combination of three time-selected laser irradiations applied to one or more body surface areas during one lipolysis treatment session. For example, an exemplary sixty-minute lypolysis treatment session may comprise three ten-minute laser irradiations about a subject's waistline area followed by three ten-minute laser irradiations about their upper abdomen area, or alternatively, by three ten minute laser irradiations about their lower back area. An exemplary 120-minute lipolysis treatment session may comprise two sets of three ten-minute laser irradiations about a subject's body torso followed by a set of three ten-minute laser irradiations about their upper thigh areas and a set of ten-minute irradiations about their upper arms.

It is within the scope of the present invention to combine the laser applicators, lipolysis systems comprising the laser applicators, and the methods for their use as exemplified herein, with other suitable devices and apparatus configured for a subject's use for physical exercising. Such suitable physical exercising devices and apparatus include equipment commonly referred to as "whole body vibration" devices that are provided with an exercise platform or surface, configured to provide controllable vibrations to a subject positioned thereon. Suitable whole body vibration devices are exemplified by the Soloflex® WBV® vibrating exercise platform (Soloflex and Soloflex WBV are registered trademarks of Soloflex Inc., Hillsboro, OR, USA), the Nobelrex K1 and K2 machines (Nobelrex K-1 Ltd., OR, USA), the Power Plate® pro5 machines (Power Plate is a registered trademark of Power Plate North America Ltd., Northbrook IL. USA), the VibePlate® platforms (VibePlate is a registered trademark of VibePlate Inc., Lincoln NE, USA) and the like. An exemplary method for combining the use of the laser applicators and lipolysis systems comprising the laser applicators of the present invention comprises securing to a target portion of a subject's body surface, at least one laser applicator configured as described herein and cooperatively communicating with a suitable laser control devise as provided with a lipolysis system of the present invention, after which the subject mounts a whole body vibration device in a suitable position. The laser irradiation treatment is then provided for a selected period of time concurrent with the delivery of vibrations to the subject by the whole body vibration device. At the conclusion of the laser irradiation treatment, the subject demounts from the whole body vibration device for re-positioning of the at least one applicator, after which, the subject remounts the whole body vibration machine for an addition period of concurrent delivery of laser irradiation from the laser applicator and vibrations from the whole body vibration device. The subject may selectively receive: (a) concurrent laser irradiation and whole body vibrations, or (b) laser irradiation only, or (c) whole body vibrations only during the course of a lipolysis treatment session with the lipolysis system of the present invention. Those skilled in these arts will understand that combining whole body vibration treatments from whole body vibration devices concurrent with lipolysis treatments by the lipolysis systems of the present invention will facilitate and enhance movement of liquefied fats from within adipose cells into the interstitial spaces, and from the interstitial spaces into the groin area where they are absorbed into the lymphatic system which will then transport the liquefied fats away from the groin area for further processing and elimination by the subject's normal physiological processes.

It is within the scope of the present invention to combine the laser applicators, lipolysis systems comprising the laser applicators, and the methods for their use as exemplified herein, with other types of non-surgical cosmetic treatments commonly employed for dissolving fats and cellulose and referred to by those skilled in these arts as mesotherapy and lipodissolve treatments. Mesotherapy typically involves multiple injections of pharmaceutical compositions and/or homeopathic compositions, and or plant extracts and/or vitamins into subcutaneous regions of a subject's body having protuberances caused by fat accumulations, while lipodissolve treatments typically involve multiple injections of phosphatidylcholine deoxycholate (PCDC) into the same target areas that mesotherapy is delivered. Mesotherapy and lipodissolve treatments are purported to cause lysis of adipose cells that are then removed from the body via its normal physiological functioning. Those skilled in these arts will understand that mesotherapy and lipodissolve treatments can be provided in combination with lipolysis treatments with the laser applicators and lipolysis systems of the present invention. For example, a series of PCDC injections can be subcutaneously administered to targeted portions of a subject's body surface. At least one or alternatively, a plurality of laser applicator according to the present invention can then be secured to an injection site for application of laser irradiation thereto with the lipolysis system of the present invention. It is suitable to secure a first laser applicator comprising a plurality of laser diodes, to an injection site and to concurrently secure a second laser applicator comprising a single laser diode, to a site about the inguinal joint area.

The examples presented below are included as embodiments of the present invention, but are not intended to limit the scope of the present invention.

The example presented below is included as an exemplary embodiment of the present invention, but is not intended to limit the scope of the present invention.

EXAMPLE 1

Methods:
(a) Clinical Trial:

Forty healthy men and women between the ages of 18-65 years of age inclusive with a body mass index (BMI) no greater than 29.9 kg/m$^2$ were randomized in a 1:1 ratio to an experimental laser treatment or to a control laser treatment.

Randomization was created from random number tables and the treatment codes were stored in sealed envelopes during the study. Subjects could not be using light sensitizing agents, undergoing photodynamic therapy or using diuretics. Subjects were required to have a stable weight, gaining or losing no more than 2.5 kg in the 6 months prior to the trial. Subjects could not be on a weight reduction regimen, and they were asked not to change their diet or exercise habits during the trial.

An exemplary lipolysis system of the present invention similar to the system illustrated in FIG. 9 was employed for the clinical trial and comprised two laser applicators each provided with four low-power laser diodes (multi-channel AlGaLnP laser diodes configured for continuous and modulated continuous power outputs in the range of about 130 mW to about 170 mW of light waves in the range of about 630 nm to about 680 nm with a modulation frequency of 0 to about 10 Hz), and a laser control device configured for controllably communicating and cooperating with the two laser applicators. Each subject received two treatments per week for a total of eight treatments over four weeks. Each treatment session lasted approximately thirty minutes. The two laser applicators were placed over the waist bilaterally in three positions and the laser was activated for ten minutes in each of these positions to encompass the waist from the back to the front. Two operators conducted each treatment session throughout the study. One operator administered the treatment, and the other operator, who was blinded to treatment allocations, obtained measurements and photographs. The operator administering the treatment remained blinded to photographic and girth measurements. Each subject was advised about the rules of blinding, and individual taking photographs and measurements could not relay this information to the subject. The operator administering the treatment did not enter the room where the photographs and measurements were obtained. A new Case Report Form was used for each measurement session and these forms were placed in a sealed envelope until data was analyzed at the end of the study. A separate person who was not involved in other aspects of the study did the blinded evaluations of the photographs.

All subjects had photographs taken at a standardized distance with standard background and lighting. Girth measurements of the waist were obtained in the manner recommended by the United States National Institutes of Health National Institute for Health guidance (NIH) at the iliac crest using a tape measure with standardized tension and parallel to the floor following the protocol outlined in the journal Obesity Research, 1998, Sep;6 Suppl. 2: 51S-209S(no authors listed). A reference point on the body for the pictures and measurements was relocated at each evaluation by measuring a distance from the floor that was determined in the first measurement at baseline. The specified measured distance was used to ensure all measurements and photographs are obtained in the same location. The camera was placed on a tripod at a fixed distance from the floor, but was adjusted to a specific height of each individual participant. Standardized waist measurements were taken at baseline, treatment session #3 and treatment session #8. Standardized photographs were taken before an after the initial treatment, t treatment session #3 and treatment session #8. Weight was measured and BMI calculated at baseline and at treatment session #8 (week 4). Blood pressure was measured at baseline, treatment session #3 and treatment session #8. Any adverse events were noted in the case report forms.

(b) In vitro Study Using Human Fat Cells

Human fat cells were prepared in two 12-well plates. Three of the cells in the plates were left as a control. Fresh plasma replaced one third of the cell culture media in another three wells. The next three wells had one third of the media replaced with fresh human white cells in suspension. The final three wells in each plate had one third of the media replaced by a combination of fresh human plasma and white blood cells. One of the plated was irradiated for ten minutes with a laser applicator comprising 4 laser diodes (multi-channel AlGaLnP laser diodes configured for continuous and modulated continuous power outputs in the range of about 130 mW to about 170 mW of light waves in the range of about 630 nm to about 680 nm with a modulation frequency of 0 to about 10 Hz), and the other was left as a non-irradiated control. The conditioned media from the four types of wells from each plate were tested for membrane attack complexes of complement (MAC) using an ELISA assay.

Results:

(a) Clinical Trial

The groups were well balanced at baseline, and the group characteristics are illustrated in Table 1. Weight and BMI did not change significantly over the 8 treatments and 4 weeks. Blood pressure did not change significantly from baseline to treatment 3, from treatment 3 to treatment 8 or from baseline to treatment 8. Each treatment with the LipoLaser gave an approximate loss of 0.4 cm to 0.5 cm in waist girth. This difference, 0.405 cm (Laser −0.59±0.708 cm vs. Placebo −0.19±0.47 cm (mean±SD), was significant (p<0.05) on the third treatment session done during week two on the completers analysis, but was not statistically significant by the intent to treat analysis. The cumulative girth loss at treatment session #3 on week two was a significant 1.74 cm

TABLE 1

Clinical trial participant data.

| Variable | Lipolysis Group | Placebo Group | P-Value |
|---|---|---|---|
| Number enrolled | 20 | 20 | |
| Gender | | | 0.0765 |
| Female | 19 | 15 | |
| Male | 1 | 5 | |
| Age (Years) | 35.1 | 38.35 | 0.3292 |
| SD | 9.11 | 11.55 | |
| Weight (kg) | 63.97 | 67.31 | 0.3705 |
| SD | 8.23 | 14.31 | |
| Height (cm) | 164.12 | 165.68 | 0.5341 |
| SD | 5.99 | 9.32 | |
| Body Mass Index (kg/m$^2$) | 23.77 | 24.35 | 0.4641 |
| SD | 2.02 | 2.87 | |
| SBP | 120.15 | 121.40 | 0.7330 |
| SD | 11.98 | 11.00 | |
| DBP | 75.35 | 75.00 | 0.8922 |
| SD | 8.23 | 8.00 | |

Values are means and standard deviation (SD)

Figure 16:
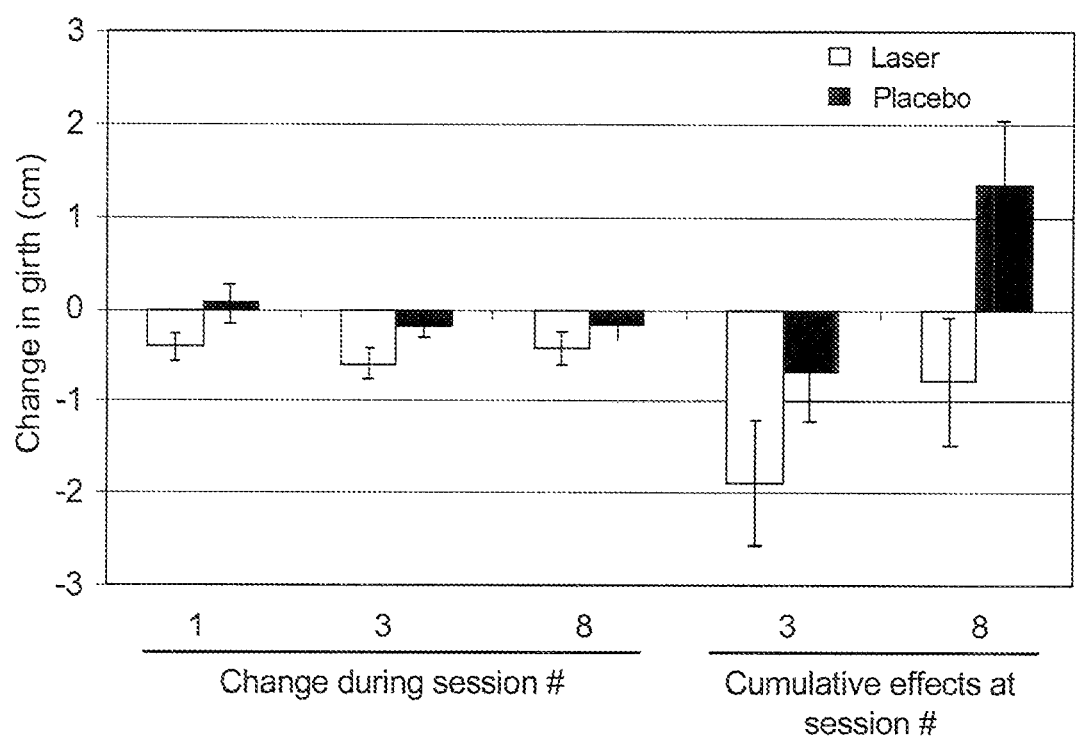
FIG. 16 is a chart showing a comparison of waistline girth loss between subjects receiving laser treatments (□) and placebo treatments (■)
Figure 17:
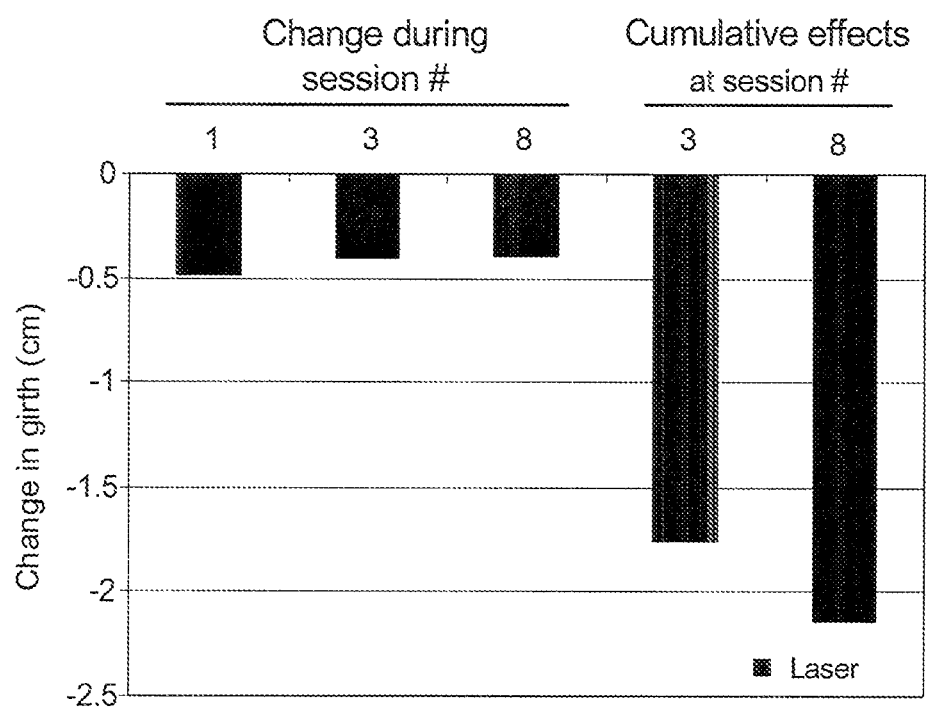
FIG. 17 is a chart showing, first, the average waistline girth loss during each laser treatment session, and second, the average waistline girth loss over the course of the combined treatment period.
Figure 18:
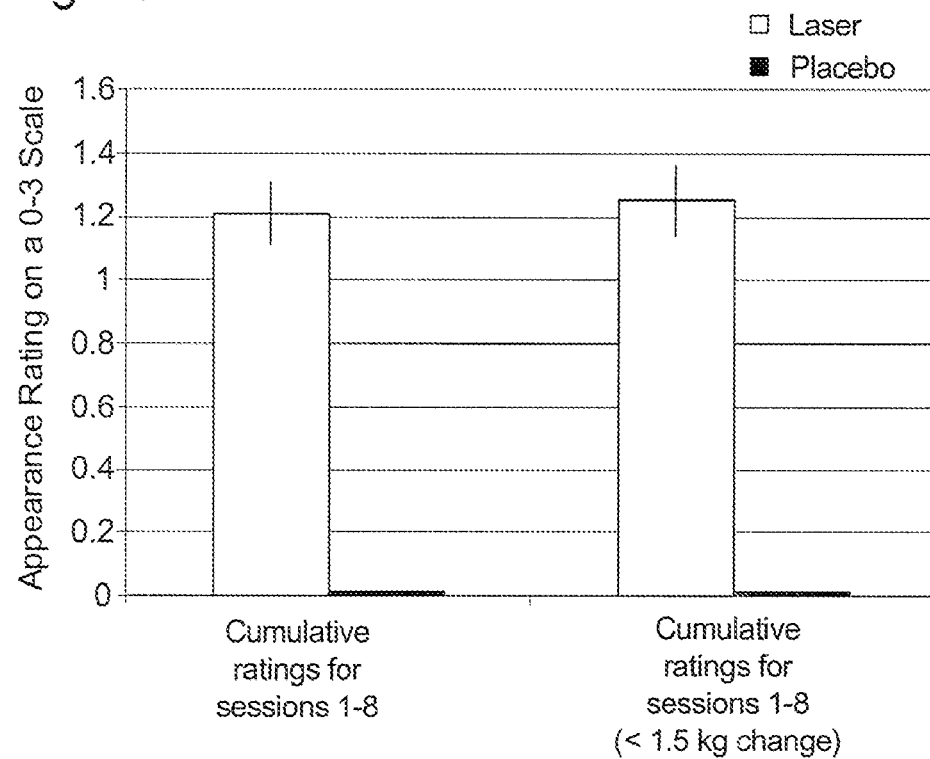
FIG. 18 is a chart showing a comparison of "blinded" appearance rating assessments performed on subjects receiving laser treatments (□) and placebo treatments (■), first, after each treatment session, and second, the averaged cumulative ratings at the end of the combined treatment period.

(Laser −1.895±2.967 cm vs. Placebo −0.16±2.458 cm) (p<0.05) on both the completers analysis and by intent to treat analysis. Cumulative girth loss at treatment session #8 (4 weeks of treatment) was 2.15 cm (Laser −0.781±2.817 cm vs. Placebo 1.353±2.644 cm) in those who maintained their weight within 1.5 kg of their baseline weight (p<0.05). The standardized pictures of the participants showed a significant 1.21 difference (Laser 1.21±0.419 vs. Placebo 0±0 cm) in appearance on a 0-3 scale favoring the LipoLaser group comparing the baseline to the week 4 (treatment 8) pictures (p<0.001). When only those participants that remained within 1.5 kg of their baseline weight were considered, the improvement in appearance increased to 1.25 (Laser 1.25±0.447 vs. Placebo 0±0) on a 0-3 scale comparing the baseline to the week 4 (treatment session #8) pictures (p<0.001). Girth losses in the laser and placebo groups at the various time points are illustrated in FIG. 16. The girth difference in the Laser group compared to the placebo group is illustrated in FIG. 17. The differences in appearance from baseline to week 4 (treatment session #8) in the whole group and the subjects who remained within 1.5 kg of their baseline weight are illustrated in FIG. 18. (One subject withdrew from the study due to scheduling conflicts. The individual was in the treatment group, and lost 0.2 cm in waist girth with the initial treatment prior to withdrawing).

(b) In vitro Study Using Human Fat Cells

The human fat cells in the non-laser treated 12-well plate remained intact. The human fat cells in culture media treated with the laser remained intact, as did the human fat cells treated with the laser in the presence of fresh human white blood cells. The fat cells treated in the presence of fresh human serum or fresh human serum combined with fresh human white blood cells released their fat. The MAC was present in both of the conditions in which the wells were treated with the laser in the presence of human serum or human serum with white blood cells.

Discussion:

A single lipolysis treatment session provided by an exemplary lipolysis system of the present invention was effective in providing giving girth loss, and repeated treatment sessions further provided between 0.4 to 0.5 cm girth loss per treatment session. This difference was statistically significant at treatment session #3 demonstrating that the effect of the lipolysis system of the present invention does not appear to diminish with repeated treatments through time. The 1.74 cm girth loss at treatment session #3 suggests that the methods of use of the lipolysis systems as described herein are cumulative in their effect on girth loss.

It is obvious that weight change over the course of treatment would change waist circumference and confound the results. The subjects selected for the study were asked not to lose or gain weight over the course of the study. Since some subjects did gain or lose a significant amount of weight over the 4 week study, the cumulative fat loss was analyzed only on those subjects whose weight was within 1.5 kg of their baseline weight. The selection of a 1.5 kg limit for weight fluctuation was based on the fact that this study was the length of a 4-week menstrual cycle minimizing the effect of menstrually-related fluid shifts in women (Robinson et al., 1965, Brit. J. Nutr. 19: 225-235).

Girth loss over the course of the study was greater than 2 cm and statistically significant. The subjects in this study were not obese and an approximate 1 inch (2.54 cm) reduction in waist girth over the course of 8 treatment sessions over a 4-week period was clinically significant. The blinded ratings of the baseline pictures compared to the treatment session #8 (week 4) pictures taken in a standardized way demonstrated an improvement in appearance that was highly statistically significant. As expected, the improvement was greater when limiting the comparison to only those subjects that remained within 1.5 kg of their baseline weight.

Thus, the laser applicators, lipolysis systems comprising the laser applicators, and methods for their use provide significant waist girth loss that is sustained over repeated treatments and is cumulative over 4 weeks of 8 treatments. This waist girth loss was almost one inch (2.54 cm) in magnitude. Therefore, the exemplary embodiments of the present invention disclosed herein provided both a clinically and statistically significant improvement in appearance.

While the exemplary laser applicators and lipolysis systems of the present invention have been described with low power laser diodes configured to produce power outputs in the range comprising about 10 mW to about 100 mW with light waves in the range of 635 nm to 680 nm, it is also within the scope of the present invention to provide laser applicators and laser applicator systems configured with combinations of low power laser diodes and medium power laser diodes having power outputs in the range of about 80 mW to about 160 mW with light waves in the range of 780 nm to 980 nm.

Although the present invention has been described with reference to certain exemplary embodiments thereof, in view of numerous changes and variations that will be apparent to persons skilled in the art, the scope of the present invention is to be considered limited solely by the appended claims.

What is claimed is:

1. A laser applicator configured for contacting a portion of a subject's body surface and controllably applying a laser irradiation thereto for the purpose of liquefying fats in adipose cells in the subcutaneous region underlying the contacted portion of the body surface, the laser applicator comprising at least one laser diode selected for emission of power outputs in the range comprising about 10 mW to about 150 mW with light waves in the range of 635 nm to 680 nm, said laser applicator communicable and cooperable with a laser control device wherein the laser applicator comprises: a printed circuit board provided with a connector configured for communicating and cooperating with a laser control device; a contact plate configured to cooperate with the printed circuit board, the contact plate provided with at least one transparent window; at least one laser diode configured to communicate with the at least one transparent window in said contact plate, the at least one laser diode interposed between the contact plate and the printed circuit board and powered by said printed circuit board; and a housing for containing therein the printed circuit board, the at least one laser diode, and the contact plate, the housing configured to contact the at least one transparent window in said contact plate with the subject's body surface.

2. A laser applicator according to claim 1, wherein the contact plate comprises a material selected from a group comprising stiff materials and flexible resilient materials.

3. A laser applicator according to claim 1, wherein the laser applicator is additionally provided with a heat absorption device interposed between the contact plate and the printed circuit board.

4. A laser applicator according to claim 3, wherein the heat absorption device is selected from a group containing a heat absorption plate interposed between the contact plate and the printed circuit board, a heat radiation plate interposed between the contact plate and the printed circuit board, and a thermal interface material coated onto a surface of the contact plate disposed toward the printed circuit board.

5. A laser applicator configured for contacting a portion of a subject's body surface and controllably applying a laser irradiation thereto for the purpose of liquefying fats in adipose cells in the subcutaneous region underlying the contacted portion of the body surface, the laser applicator comprising a first laser diode selected for emission of power outputs in the range comprising about 10 mW to about 150 mW with light waves in a first range of 635 nm to 680 nm; a second laser diode selected for emission of light waves in a second range, wherein light waves of the second range are longer in wavelength than light waves of the first range; said laser applicator communicable and cooperable with a laser control device wherein said laser applicator additionally comprises a vacuum suction device configured to engage a target portion of the subject's body surface, and wherein the vacuum suction device is configured to controllably provide a suction force to the target portion of the subject body's surface concurrently with irradiation by the first laser diode and the second laser diode.

6. A laser applicator according to claim 5 wherein the second laser diode is selected for emission of power outputs in the range comprising about 80 mW to about 160 mW with light waves in the range of 780 nm to 980 nm.

7. A laser applicator configured for contacting a portion of a subject's body surface and controllably applying laser irradiation thereto for the purpose of liquefying fats in adipose cells in the subcutaneous region underlying the contacted portion of the body surface, the laser applicator comprising: at least one laser diode selected for emission of power outputs in the range comprising about 10 mW to about 150 mW with light waves in the range of 635 nm to 680 nm; a printed circuit board provided with a connector configured for communicating and cooperating with a laser control device; a housing comprising a contact plate for contacting the portion of the body surface; a heat absorption device between the contract plate and the printed circuit board; wherein the at least one laser diode is interposed between the contact plate and the printed circuit board and powered by the printed circuit board; and wherein the housing contains the at least one laser diode, the printed circuit board, and the heat adsorption device.

* * * * *